United States Patent [19]

Clark et al.

[11] Patent Number: 5,732,871
[45] Date of Patent: Mar. 31, 1998

[54] SURGICAL STAPLING INSTRUMENT WITH ARTICULATED STAPLING HEAD ASSEMBLY ON ROTATABLE AND FLEXIBLE SUPPORT SHAFT

[75] Inventors: George A. Clark, East Windsor; Malcolm C. Burwell, Princeton; John A. Gola, Bordentown; Christopher Robinson, Lawrenceville; Fred E. Snyder, Princeton Junction, all of N.J.

[73] Assignee: Ethicon, Inc., Somerville, N.J.

[21] Appl. No.: 433,660

[22] Filed: May 4, 1995

Related U.S. Application Data

[62] Division of Ser. No. 162,737, Dec. 6, 1993, Pat. No. 5,465,894.

[51] Int. Cl.$^6$ ............................................. A61B 17/072
[52] U.S. Cl. .................................. 227/175.1; 227/178.1; 227/19
[58] Field of Search .......................... 227/19, 175.1, 227/176.1, 177.1, 178.1, 179.1, 180.1, 181.1

[56] References Cited

U.S. PATENT DOCUMENTS

| | | | |
|---|---|---|---|
| 3,080,564 | 3/1963 | Strekopitov et al. | 1/50 |
| 3,275,211 | 9/1966 | Hirsch et al. | 227/124 |
| 3,315,863 | 4/1967 | O'Dea | 227/19 |
| 3,589,589 | 6/1971 | Akopov | 227/153 |
| 4,354,628 | 10/1982 | Green | 227/19 |
| 4,383,634 | 5/1983 | Green | 227/19 |
| 4,402,445 | 9/1983 | Green | 227/19 |
| 4,473,077 | 9/1984 | Noiles et al. | 128/305 |
| 4,508,253 | 4/1985 | Green | 227/19 |
| 4,527,724 | 7/1985 | Chow et al. | 227/8 |
| 4,566,620 | 1/1986 | Green et al. | 227/19 |
| 4,591,085 | 5/1986 | Giovanni | 227/8 |
| 4,610,383 | 9/1986 | Rothfuss et al. | 227/19 |
| 4,728,020 | 3/1988 | Green et al. | 227/19 |
| 4,869,414 | 9/1989 | Green et al. | 227/19 |
| 4,907,591 | 3/1990 | Vasconcellos et al. | 227/19 X |
| 4,938,408 | 7/1990 | Bedi et al. | 227/8 |
| 4,941,623 | 7/1990 | Pruitt | 227/19 |
| 5,100,042 | 3/1992 | Gravener et al. | 227/176.1 |
| 5,116,349 | 5/1992 | Aranyi | 227/19 X |
| 5,137,198 | 8/1992 | Nobis et al. | 227/19 |
| 5,219,111 | 6/1993 | Bilotti et al. | 227/175.1 |
| 5,271,543 | 12/1993 | Grant et al. | 227/179 |
| 5,312,023 | 5/1994 | Green et al. | 227/19 X |
| 5,326,013 | 7/1994 | Green et al. | 227/19 X |
| 5,405,073 | 4/1995 | Porter | 227/175.1 |
| 5,470,006 | 11/1995 | Rodak | 227/176.1 |

Primary Examiner—Joseph J. Hail, III
Assistant Examiner—Jay A. Stelacone
Attorney, Agent, or Firm—Paul A. Coletti

[57] ABSTRACT

An improved surgical instrument is provided for applying surgical fasteners, such as staples, to human tissue which is particularly suited for applying one or more rows of fasteners across a tissue lumen. The surgical instrument can be used in thoracic and abdominal surgical procedures where access to the surgical site is restricted. The surgical instrument includes an articulated fastener applying assembly mounted on a rotatable and flexible support shaft assembly to provide more convenient access to restricted surgical sites. The fastener applying assembly has a compact construction including a fixed jaw which supports a fastener cartridge and a movable jaw which supports an anvil for clamping the tissue therebetween. The fastener applying assembly includes a pin placement mechanism which is actuated by the movable jaw to control the movement of a tissue retaining pin on the fixed jaw. A dual cam mechanism is provided for driving the fasteners into the tissue clamped between the anvil and the fastener cartridge. The instrument has an actuator handle assembly with an improved actuator mechanism for closing the jaws and driving the fasteners into the tissue.

10 Claims, 15 Drawing Sheets

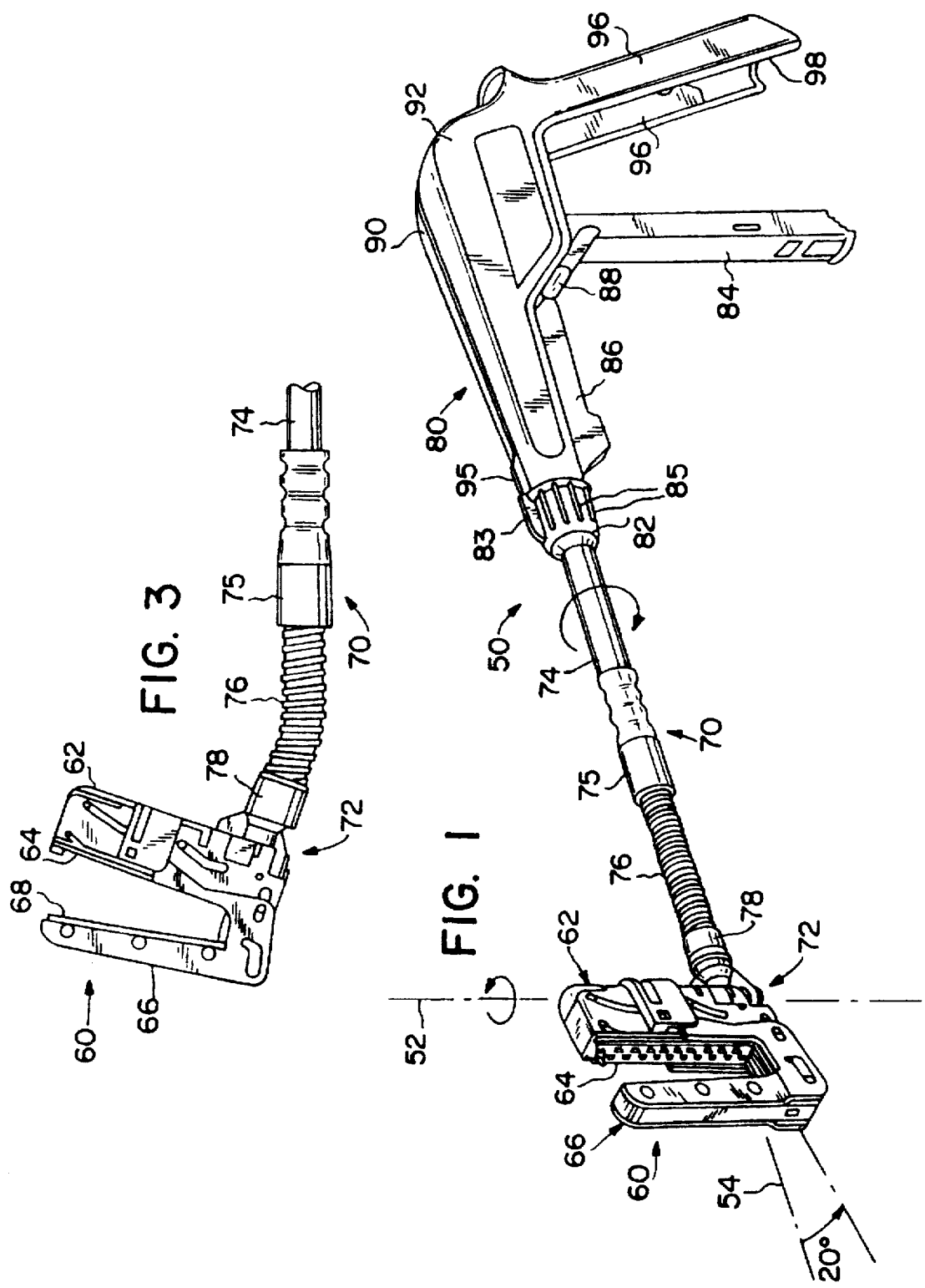

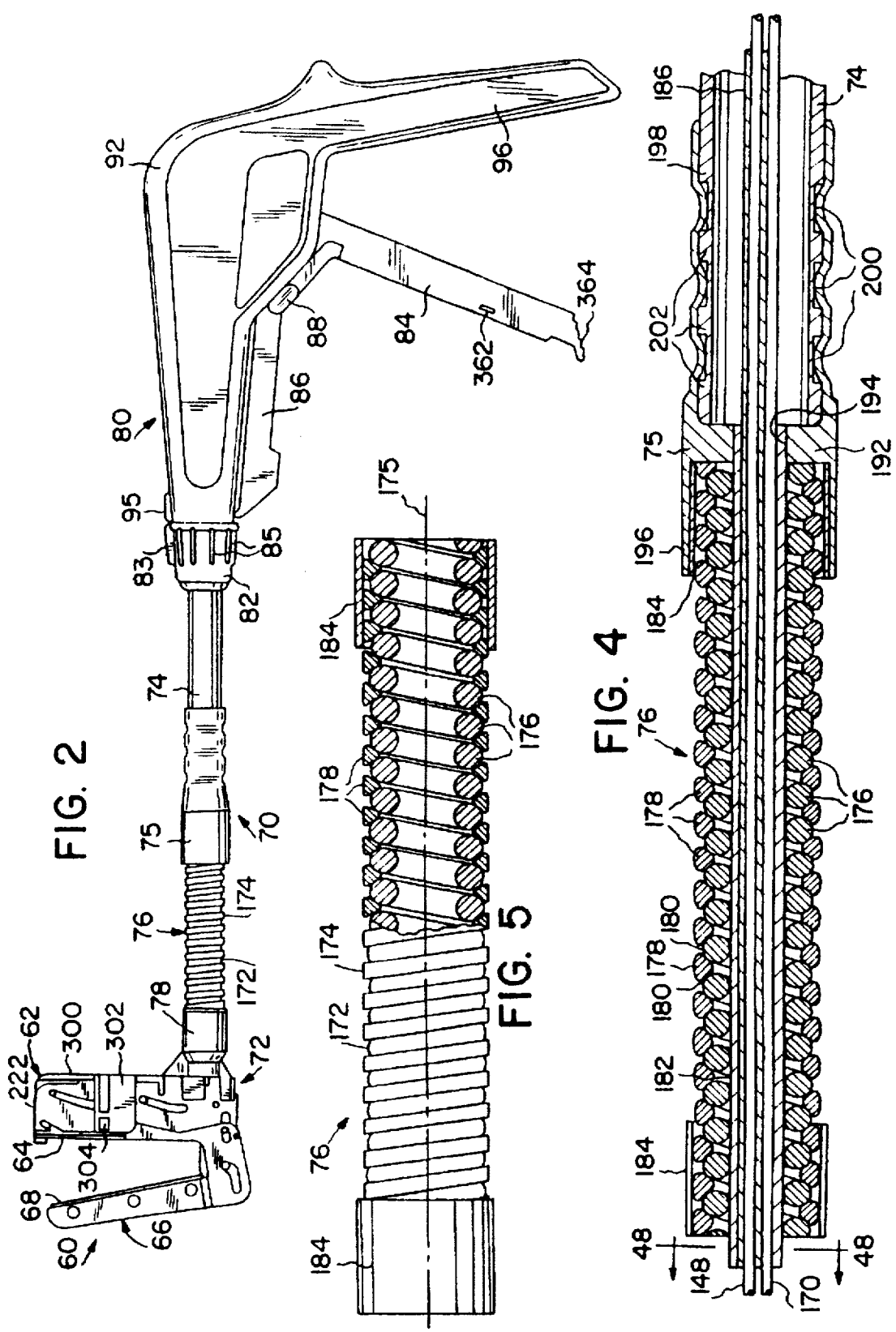

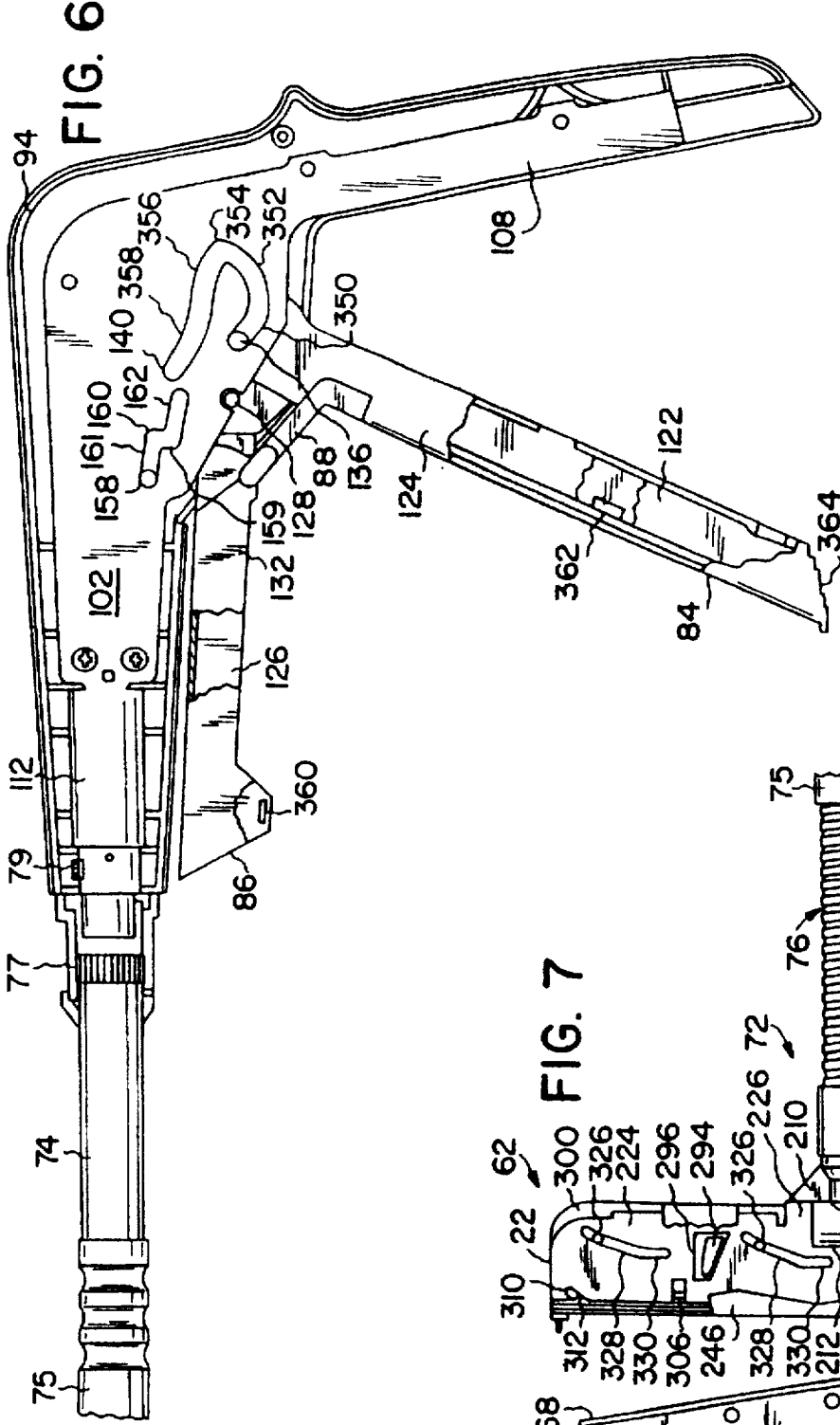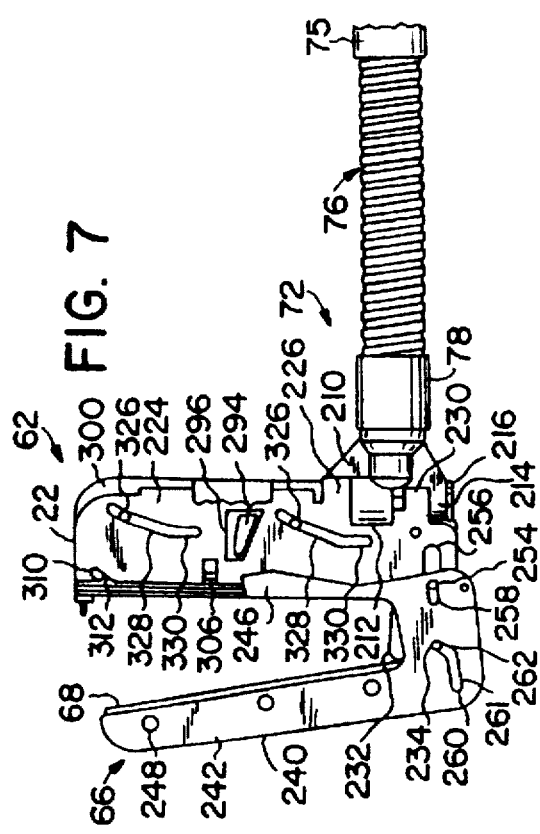

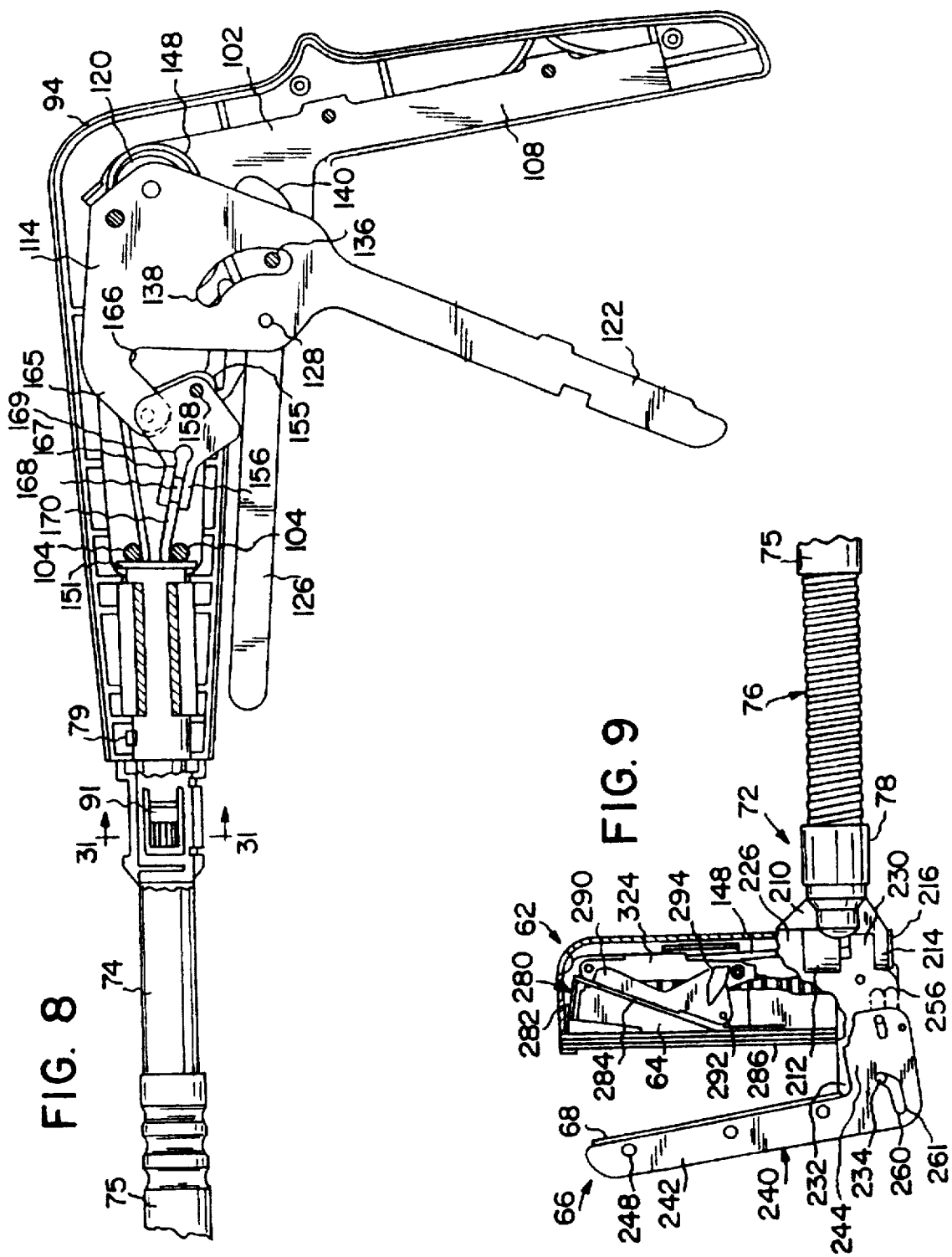

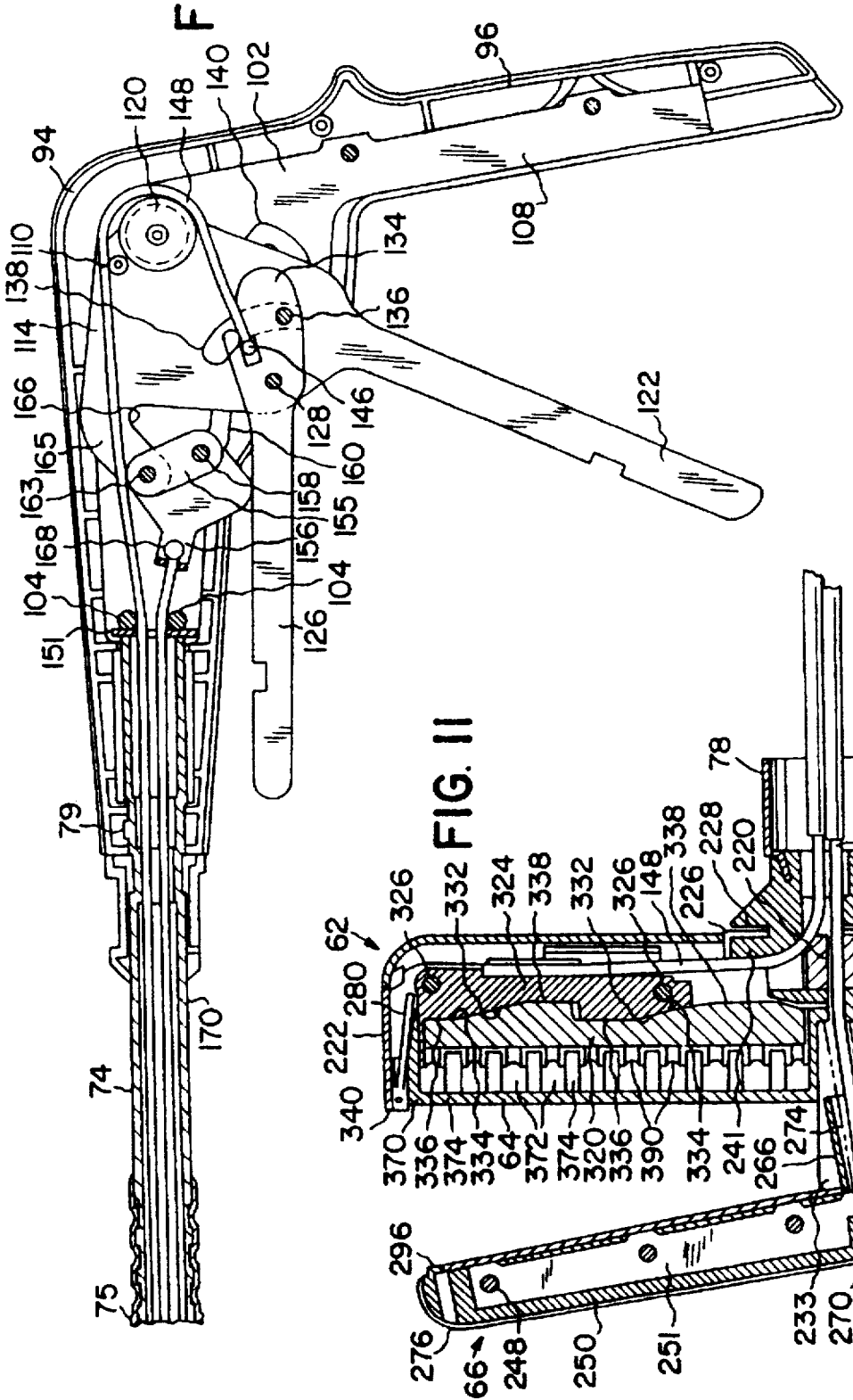

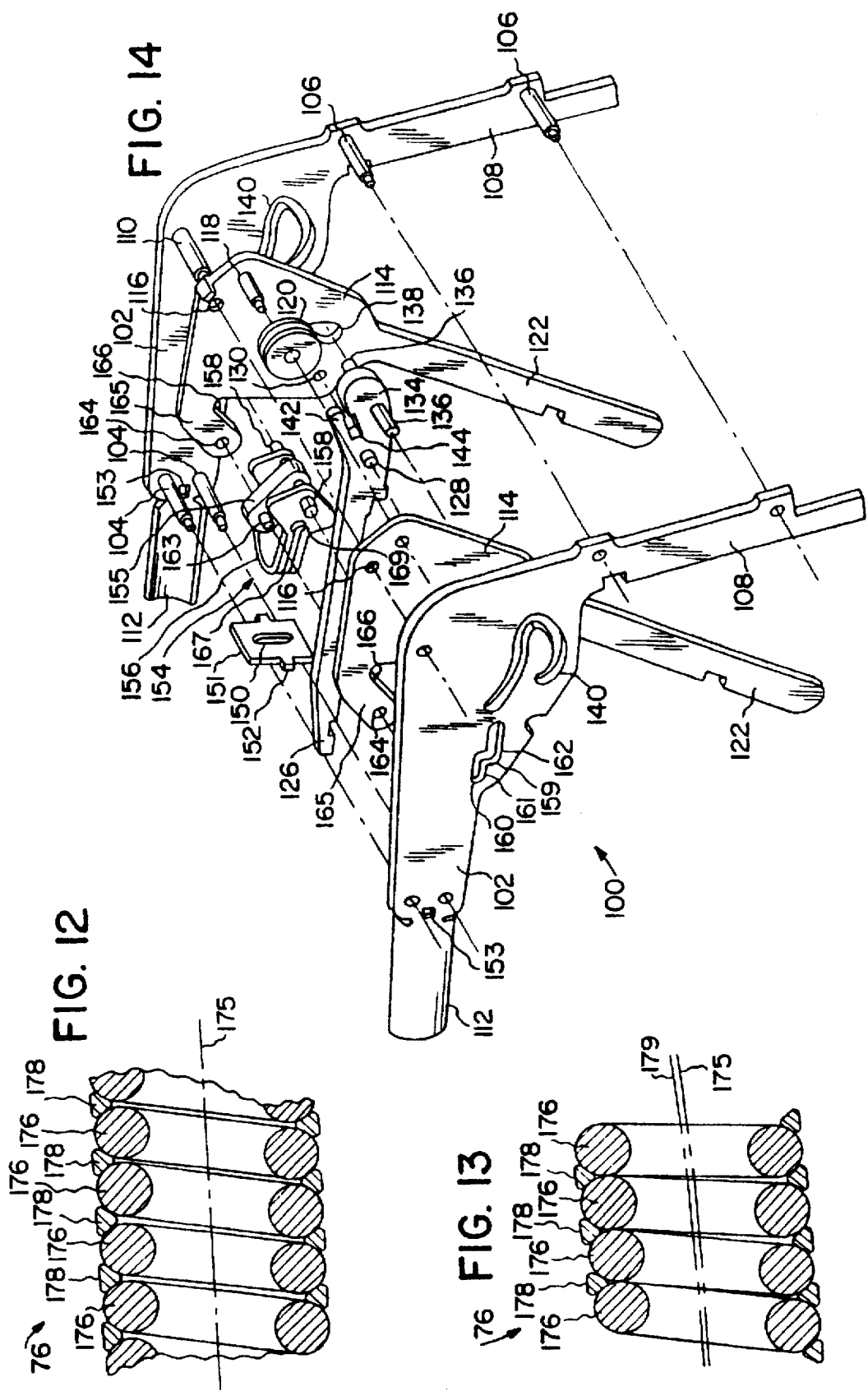

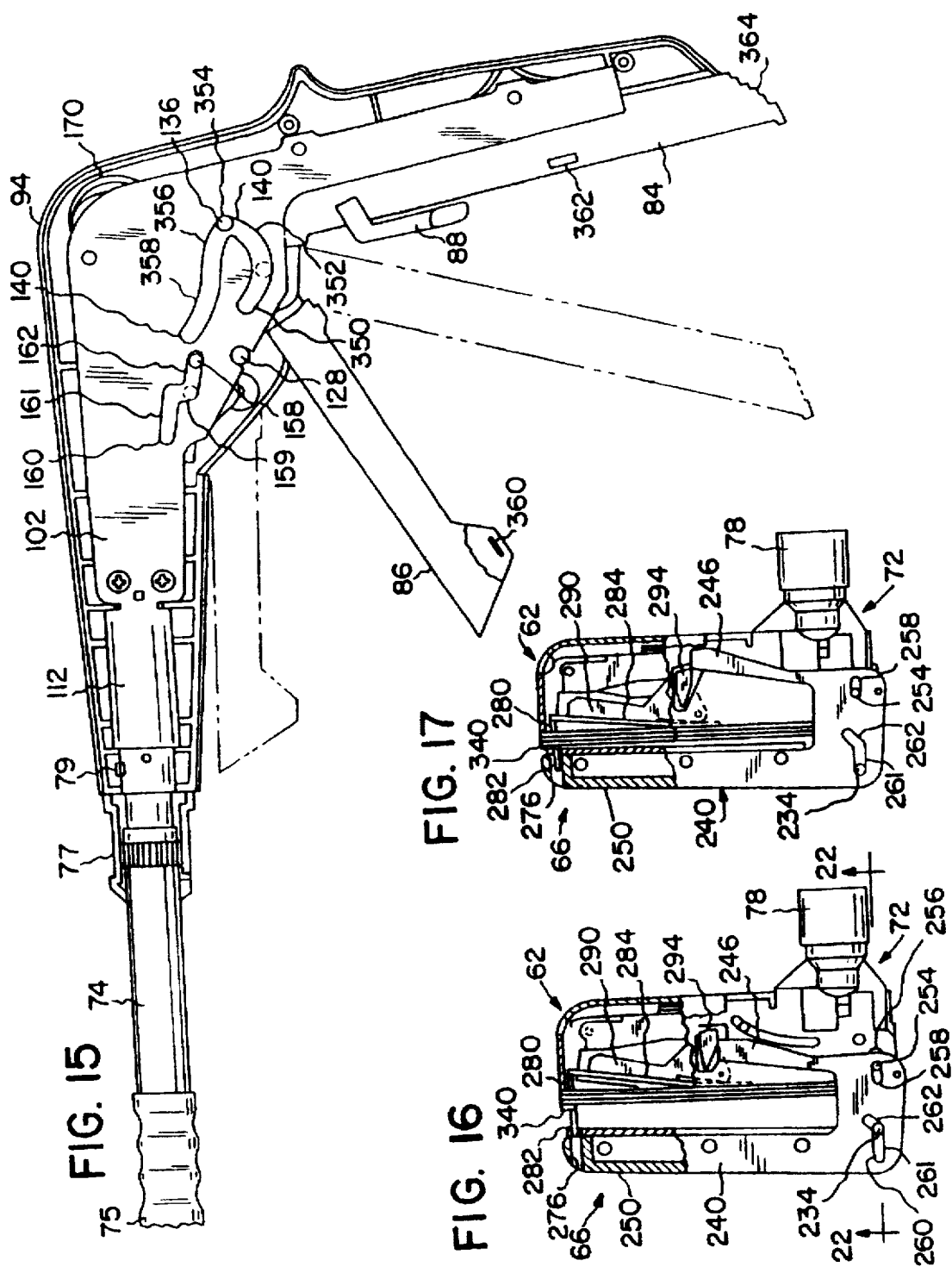

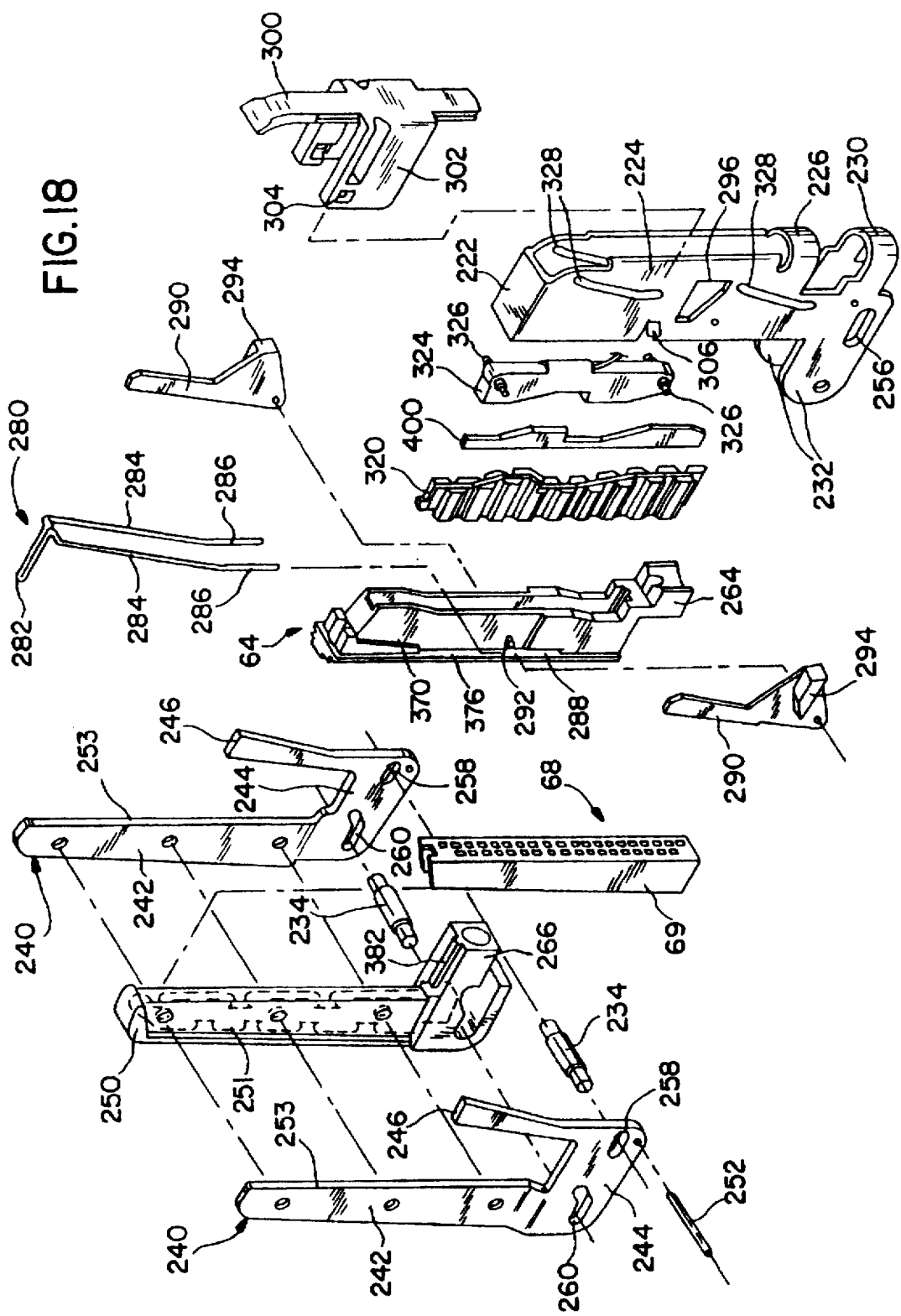

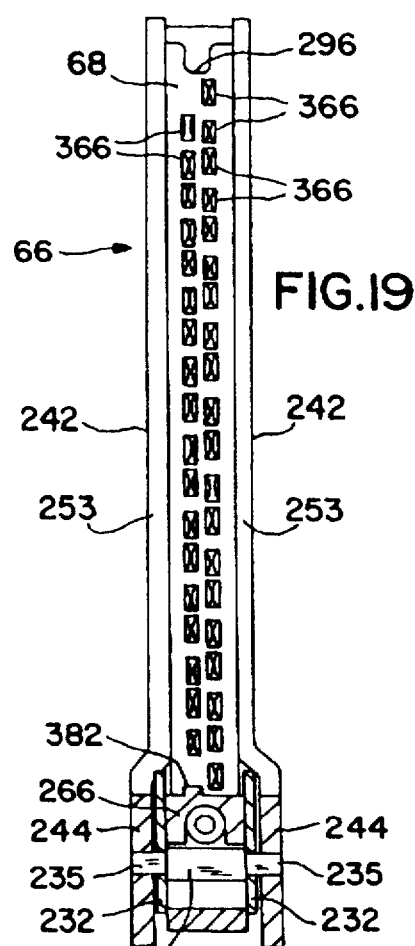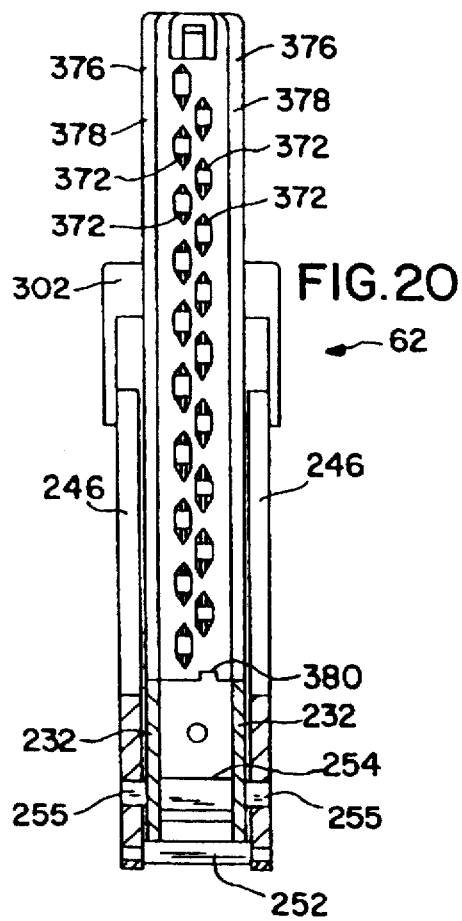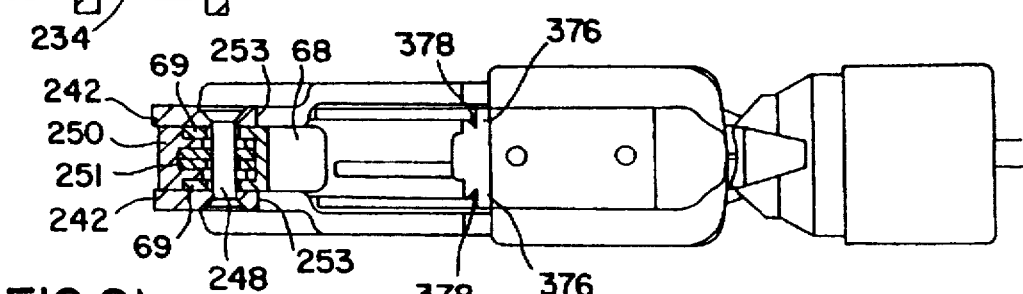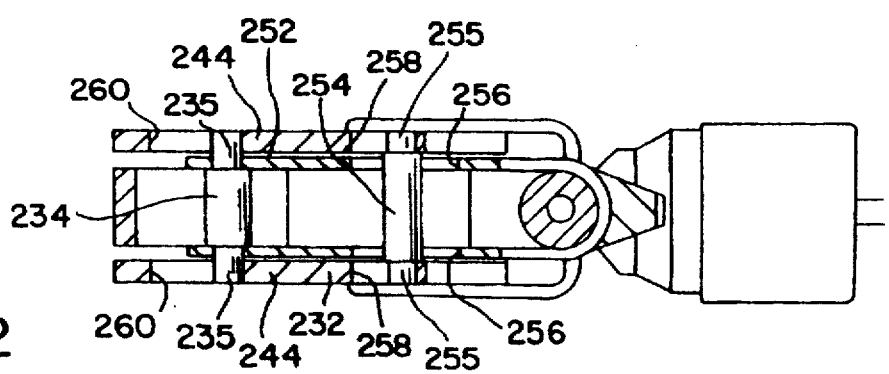

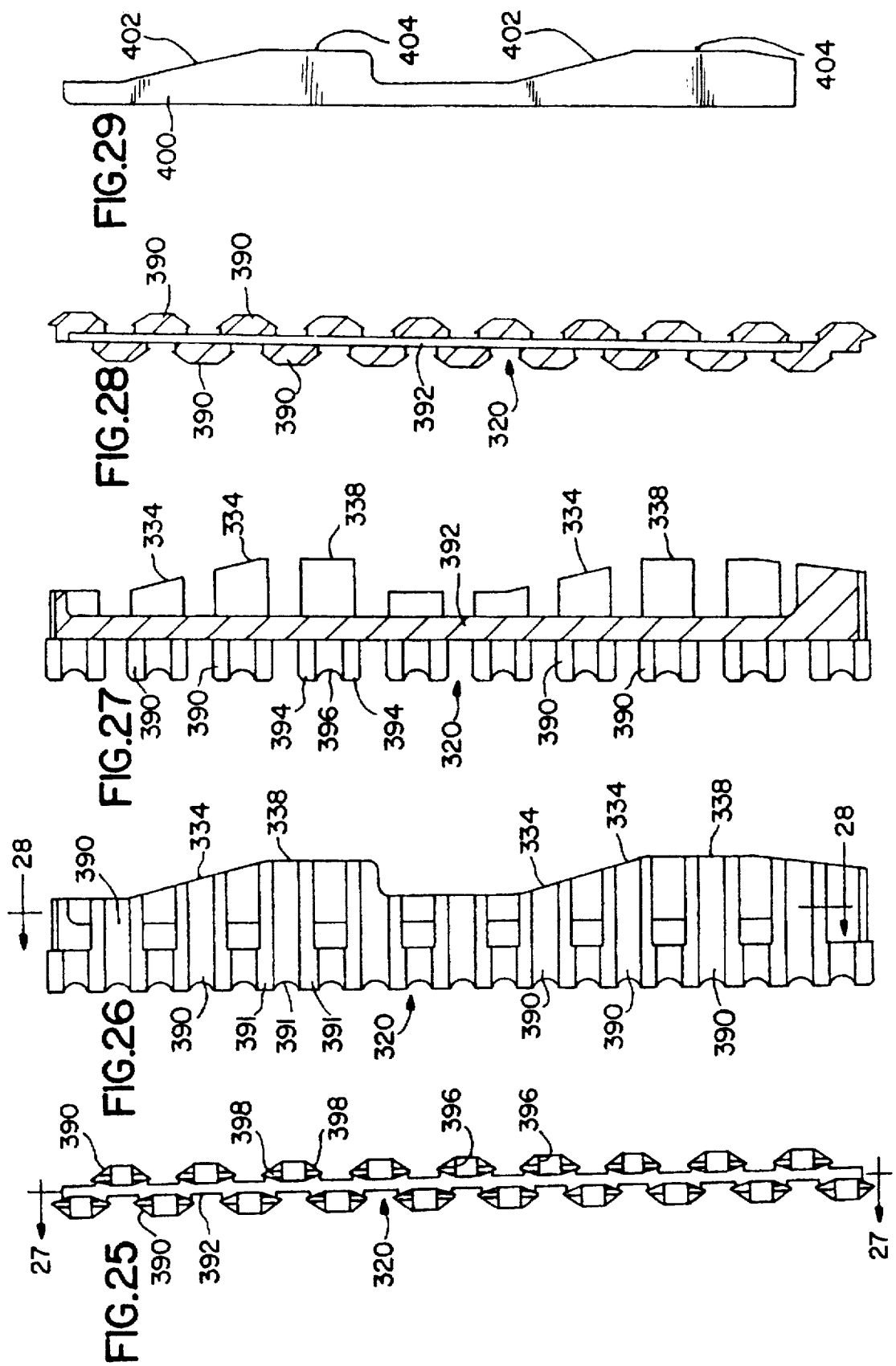

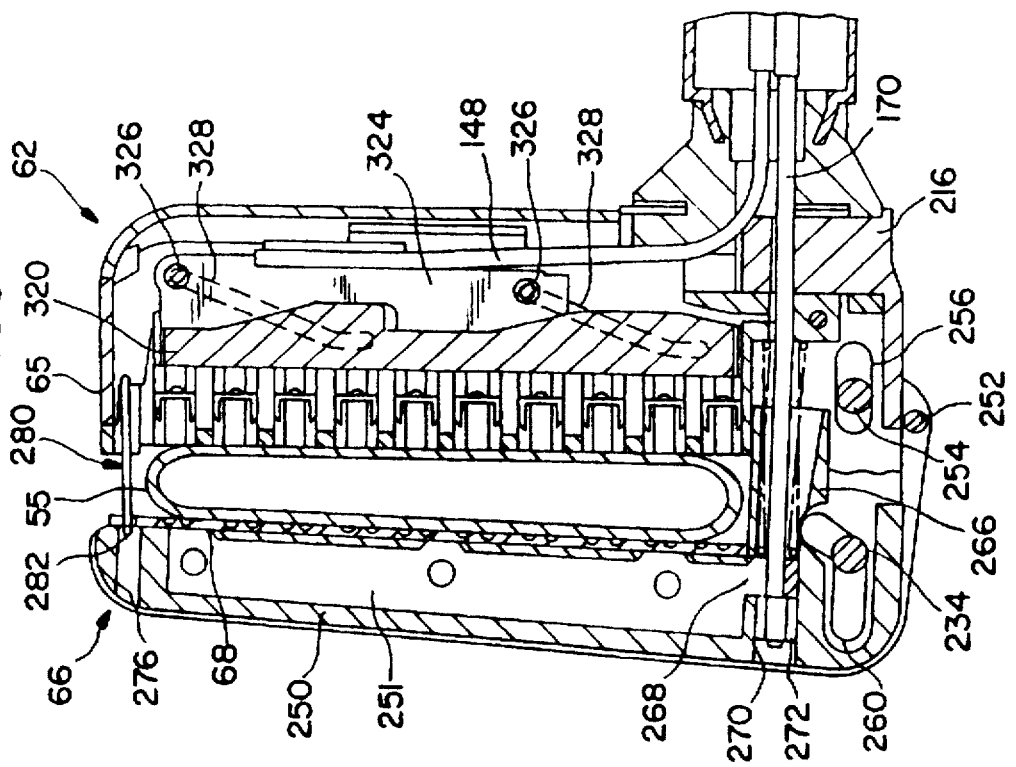
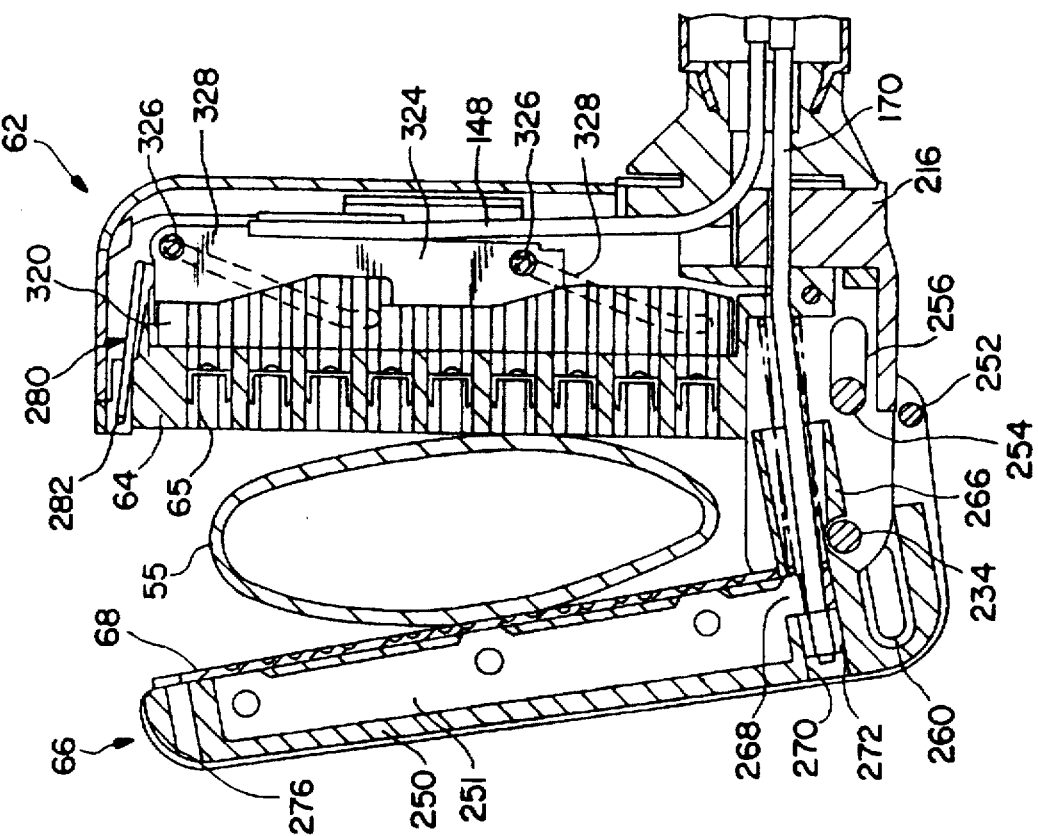

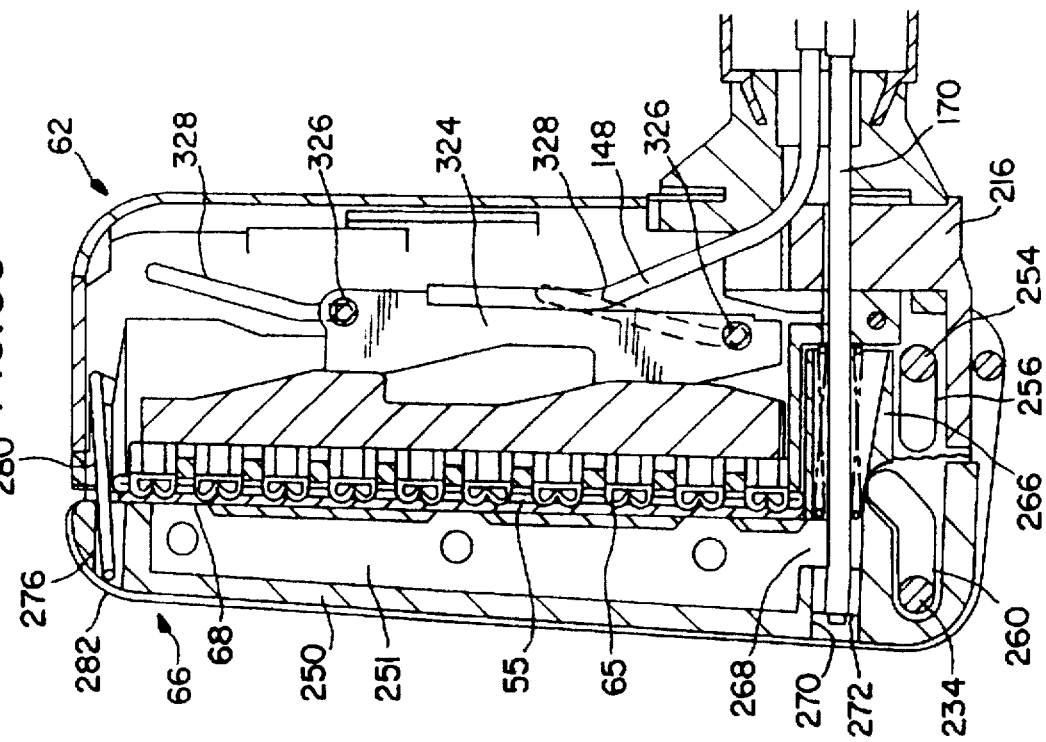
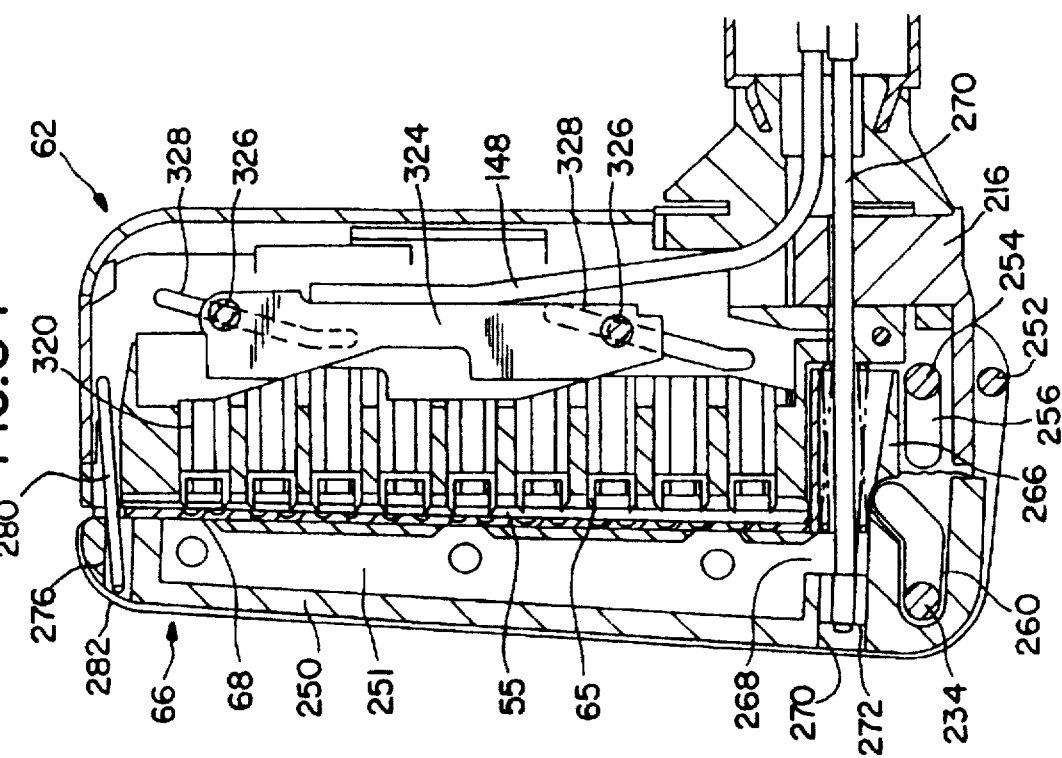

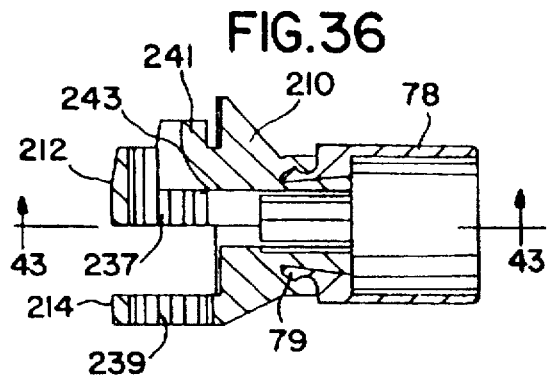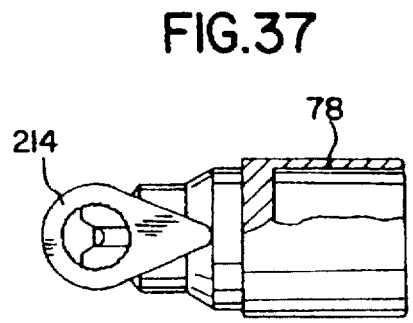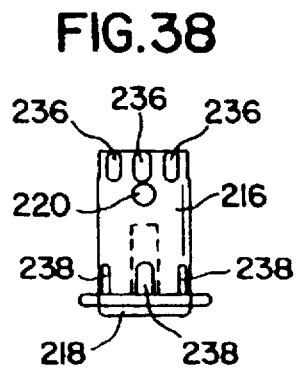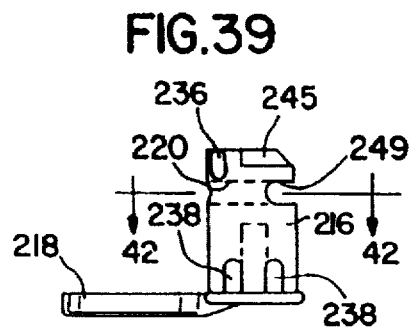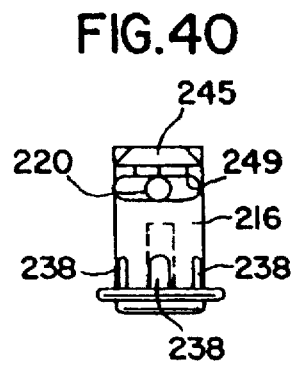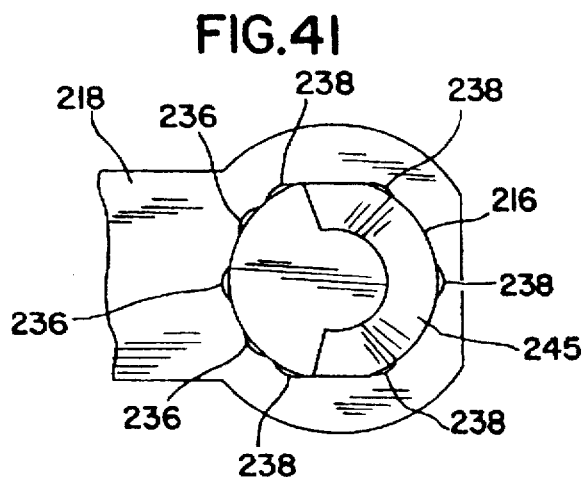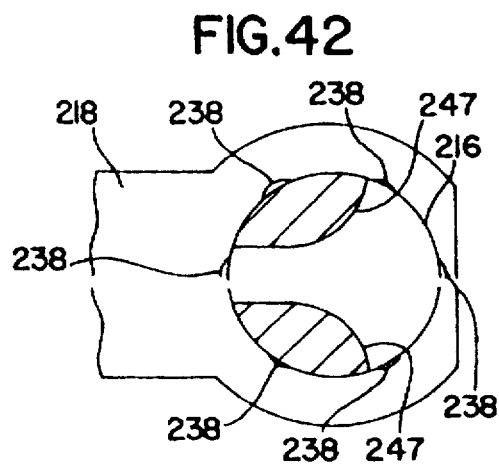

5,732,871

1

SURGICAL STAPLING INSTRUMENT WITH ARTICULATED STAPLING HEAD ASSEMBLY ON ROTATABLE AND FLEXIBLE SUPPORT SHAFT

This is a division of application Ser. No. 08/162,737, filed Dec. 6, 1993, now U.S. Pat. No. 5,465,894, which is hereby incorporated by reference.

FIELD OF THE INVENTION

The present invention generally relates to a surgical instrument for applying surgical fasteners to tissue and, more particularly, to a surgical stapling instrument with an articulated stapling head assembly mounted on a rotatable and flexible support shaft to provide more convenient access to restricted surgical sites. Also, this invention relates to a linear surgical stapling instrument including an improved stapling head assembly which is compact in construction and to an improved actuator handle assembly for closing and firing the stapling head assembly.

BACKGROUND OF THE INVENTION AND PRIOR ART

In recent years, there has been an increasing number of surgeons using surgical staples, rather than conventional sutures. This is true because the use of surgical staples and surgical stapling instruments has made many difficult procedures much simpler to perform. Of more importance, however, is that the use of surgical staples significantly reduces the time required for most procedures, and therefore reduces the length of time which the patient must be maintained under anesthetic. Many types of surgical stapling instruments have been devised for different surgical procedures.

The present invention is directed to a surgical instrument for applying surgical fasteners to internal organs and tissues such as the lung, esophagus, stomach, duodenum, and intestines. The invention is embodied in a linear surgical stapler which permits access to restricted surgical sites, e.g., the pelvic area of the human body.

In its earliest form, the linear surgical stapling instrument was a permanent, multi-use instrument and the surgical staples were manually loaded into the instrument one at a time. An example of a surgical stapling instrument of this type is disclosed in U.S. Pat. No. 3,080,564. This type of instrument was, in general, complex in construction, expensive to manufacture, heavy, bulky and difficult to both load the surgical staples and to clean and sterilize after each use. A subsequent improvement in linear surgical stapling instruments was the provision of presterilized, disposable loading units or staple cartridges. U.S. Pat. Nos. 3,275,211, 3,315,863 and 3,589,589 disclose examples of permanent, multi-use linear instruments having replaceable staple cartridges.

Several types of surgical fastener applying instruments are known for applying surgical fasteners to body tissue clamped between relatively movable fastener holding and anvil portions of the instrument. The surgical fasteners may be metal staples as shown, for example, in U.S. Pat. No. 3,275,211, or consist of non-metallic resinous materials as shown, for example, in U.S. Pat. 4,402,445. In the case of metal staples, the staple legs are typically driven through the tissue and formed by the anvil to secure the staples in the tissue. In the case of non-metallic fasteners, each fastener may initially consist of two separate parts, i.e., a fastener part disposed in the fastener holding part of the apparatus, and a retainer part disposed in the anvil part of the apparatus.

2

The leg or legs of the fastener parts are driven through the tissue and interlock with the retainer parts to secure the fasteners in the tissue. Although most surgical staples are biologically inert and remain permanently in the body, biologically absorbable metal surgical staples are known. Surgical fasteners of non-metallic resinous materials can also be made either biologically absorbable or non-absorbable.

The surgical instrument of the present invention is not limited to use with any particular type or form of fasteners. The various surgical fasteners mentioned above represent examples of the types of fasteners which can be used with the instrument of the present invention. Thus, as used herein, surgical fastener is meant to be generic to all of the above fasteners, including both staples and two-part devices. Similarly, as used herein, fastener holder and anvil are terms which are generic to surgical instruments for applying the above types of fasteners.

In the prior instruments disclosed in U.S. Pat. Nos. 3,275,211 and 4,402,445 for applying surgical fasteners to tissue clamped between the fastener holding and anvil portions of the instrument, a distal fastener applying assembly is rigidly connected to the proximal actuator portion of the instrument. More recently, however, there has been increasing interest in instruments in which the connection between the fastener applying assembly and the actuator assembly is not completely rigid. U.S. Pat. No. 4,473,077, for example, shows a surgical stapler in which the shaft assembly connected between the fastener applying and actuator assemblies is transversely flexible in a single plane.

Also, in view of rising hospital costs, there has been an ever increasing interest in disposable surgical stapling instruments to eliminate as much work as possible, i.e., disassembly, cleaning, reassembly, sterilization and the like, and to be more efficient, while at the same time, not having to compromise the surgical procedures. U.S. Pat. Nos. 4,354,628, 4,383,634 and 4,527,724, for example, each disclose disposable linear surgical stapling instruments.

U.S. Pat. Nos. 4,566,620, 4,728,020 and 4,869,414, disclose other examples of instruments for applying surgical fasteners to tissue clamped between the fastener holding and anvil portions of the instrument. An articulated surgical fastener applying apparatus is disclosed in U.S. Pat. No. 4,566,620 in which the fastener applying assembly is rotatably mounted at the distal end of a longitudinal shaft assembly by a joint for allowing rotation of the fastener applying assembly relative to the actuator assembly about each of three mutually orthogonal axes. U.S. Pat. Nos. 4,728,020 and 4,869,414 each disclose an articulated surgical fastener applying apparatus including a fastener applying assembly mounted at the distal end of a longitudinal shaft assembly for pivotal movement about an axis transverse to the longitudinal axis of the shaft assembly which is substantially inflexible about all other axes parallel to the transverse axis. The shaft assembly is rotatably mounted on a proximal actuator assembly to allow rotation of the fastener applying assembly relative to the actuator assembly about the longitudinal axis of the shaft assembly. One drawback of these instruments is that the access of the fastener applying assembly into the pelvic area is restricted by the relatively large dimensions of the fastener holding portions of the instruments. Also, the fastener applying assembly of these instruments includes protruding latch buttons and alignment pin carriers which further limit the access of the fastener applying assembly into the pelvic area.

Additional examples of surgical instruments including a fastener applying assembly provided with relatively movable fastener holding and anvil portions are disclosed in U.S. Pat. Nos. 4,591,085 and 4,941,623. The instrument disclosed in U.S. Pat. No. 4,591,085 includes a trigger interlocking mechanism which precludes the actuation of the trigger until an appropriate gap is set between the jaws of the instrument.

U.S. Pat. No. 4,938,408 discloses a surgical stapling instrument including a rotatable support shaft on which a stapler head is rotatably mounted for rotation about an axis normal to the axis of the support shaft. U.S. Pat. No. 5,137,198 discloses a linear surgical stapling instrument including a fast jaw closure mechanism and a trigger safety device.

In co-pending U.S. patent application Ser. No. 832,299, filed on Feb. 7, 1992, now U.S. Pat. No. 5,271,543, entitled "Surgical Anastomosis Stapling Instrument With Flexible Support Shaft And Anvil Adjusting Mechanism", assigned to the same assignee as the present invention, a surgical stapling instrument including a flexible shaft assembly is disclosed. The flexible shaft assembly comprises a pair of elongated helical elements which are concentrically wound together with the coils of the first helical element alternately interspersed with the coils of the second helical element. Each coil of the first helical element has a round cross section and each coil of the second helical element has a triangular cross section provided with sloped surfaces which slidably engage the adjacent round coils. There is, however, no disclosure of any mechanism to limit the bending of the flexible shaft assembly.

SUMMARY OF THE INVENTION

The present invention achieves an improved surgical instrument for applying surgical fasteners, such as staples, to human tissue which is particularly suited for applying one or more rows of fasteners across a tissue lumen to produce a fluid tight closure of the lumen. The surgical instrument of this invention is intended for use in thoracic and abdominal surgical procedures in which single fire surgical staplers are currently used and where access to the surgical site is restricted. For example, the surgical instrument can be used in the following types of procedures: (1) a double stapling technique, especially for a low anterior re-section, (2) closure of the bronchus during a lobectomy or pneumonectomy, (3) closure of the esophagus in esophageal procedures, and (4) closure of the pulmonary blood vessels during a lobectomy or pneumonectomy.

The surgical instrument of the present invention comprises a shaft assembly including a support shaft section and a flexible shaft section for mounting a fastener applying assembly on an actuator handle assembly. The fastener applying assembly includes a fastener holder for applying one or more surgical fasteners, an anvil for clamping the tissue against the anvil holder, and a driver for driving the fasteners from the fastener holder into the tissue clamped by the anvil against the fastener holder. The actuator handle assembly includes means for actuating the driver. The flexible shaft section of the shaft assembly is adapted to be bent in any radial direction relative to the longitudinal axis of the shaft assembly, e.g., into a curved configuration. The flexible shaft section is designed to retain its bent or curved shape and to resist deflection when the surgical instrument is operated. The flexible shaft section is limited to a predetermined range of bending angles relative to the longitudinal axis of the shaft assembly.

In a preferred embodiment of the surgical instrument, the flexible shaft section is located at the distal end of the shaft assembly adjacent to the fastener applying assembly. A pivot connection is provided at the distal end of the shaft assembly for supporting the fastener applying assembly to pivot about an axis transverse to the longitudinal axis of the shaft assembly. The pivot connection includes detent means for maintaining the fastener applying assembly in predetermined angular orientations relative to the longitudinal axis of the shaft assembly. Preferably, the shaft assembly is rotatable about its axis to orient the fastener applying assembly in different angular orientations relative to the actuator handle assembly. The instrument includes means for locking the shaft assembly in different angular orientations relative to the actuator handle assembly.

By bending the flexible shaft section into an appropriate configuration, the surgeon can insert the fastener applying assembly at a surgical site, e.g., into the pelvic area, where access is restricted. By rotating the shaft assembly on its axis and pivoting the fastener applying assembly about the transverse axis of the pivot connection, the surgeon can locate the fastener applying assembly in a convenient orientation for clamping the tissue between the fastener holder and the anvil and for actuating the surgical instrument without interference from the viscera or the body wall.

In accordance with another aspect of the invention, a surgical stapling instrument for applying one or more surgical staples to tissue comprises a stapling head assembly including a first jaw which supports a staple holder for receiving one or more surgical staples, a second jaw which supports an anvil for clamping the tissue against the staple holder when the jaws are closed, and a staple driver for driving the staples from the staple holder into the tissue and against the anvil, an actuator handle assembly including a jaw closure lever for closing the jaws to move the anvil into a tissue clamping position and a staple firing trigger for actuating the staple driver, and a shaft assembly for mounting the stapling head assembly on the actuator handle assembly. The stapling head assembly includes a tissue retaining pin mounted inside one of the jaws which is movable from a retracted position within the one jaw when the jaws are open to an extended position engaging the other jaw when the jaws are closed. The other jaw includes actuator means for moving the tissue retaining pin between the retracted and extended positions.

Preferably, the tissue retaining pin is mounted on a cantilever spring arm which supports the tissue retaining pin for movement between the retracted and extended positions. A pin placement arm is pivotally mounted inside the same jaw which supports the tissue retaining pin for engaging the cantilever spring arm and moving the tissue retaining pin from the retracted position to the extended position. The pin placement arm includes a cam projecting laterally therefrom and extending through a window formed in the jaw. A cam actuator finger is provided on the other jaw for engaging the cam when the jaws are closed to pivot the pin placement arm and move the retaining pin from the retracted position to the extended position.

In the case of a linear surgical stapler, the tissue retaining pin, the cantilever spring arm, and the pin placement arm are mounted inside the proximal jaw which supports the staple holder. The laterally projecting cam on the pin placement arm is actuated by the cam actuator finger mounted on the distal jaw which supports the anvil. Also, it is contemplated that the tissue retaining pin, the spring arm and the pin placement arm can be mounted on the distal jaw and the cam actuator finger can be mounted on the proximal jaw.

No portion of the tissue retaining pin protrudes from the stapling head assembly with the anvil and staple holder in the open or unclamped position. Thus, the tissue retaining pin does not interfere with the placement of the stapling head assembly in a desired orientation at a restricted surgical site. Also, no portion of the actuator mechanism for the tissue retaining pin, except for the laterally projecting cam, protrudes from the stapling head assembly. Thus, the pin actuator mechanism does not interfere with the desired placement of the stapling head assembly at the restricted surgical site.

In accordance with another aspect of the invention, the surgical stapling instrument includes a closure cable extending through the shaft assembly for pulling the distal jaw toward the proximal jaw when the jaw closure lever is actuated, a firing cable extending through the shaft assembly for actuating the staple driver when the staple firing trigger is actuated, and a pivot connection at the distal end of the shaft assembly for supporting the stapling head assembly to pivot about an axis transverse to the longitudinal axis of the shaft assembly which is adapted to slidably receive the closure cable and to provide a path of substantially constant length for the closure cable as the stapling head assembly is pivoted relative to the shaft assembly. In addition, each of the cables is adapted to maintain a substantially constant length when the shaft assembly is rotated about its axis. Preferably, each of the cables has a multi-filament counter-twisted construction to resist changes in length when the shaft assembly is rotated about its axis. In a preferred embodiment of the cable construction, each of the cables comprises a plurality of strands twisted together in a first helical direction, and each of the strands comprises a plurality of filaments twisted together in a second helical direction opposite to the first helical direction.

Another feature of the invention relates to a cam actuator mechanism for actuating the staple driver with different mechanical advantages when the staple firing trigger is actuated. The cam actuator mechanism is adapted to actuate the staple driver with a first mechanical advantage over a first portion of the stroke of the staple firing trigger and with a second mechanical advantage over a second portion of the stroke of the staple firing trigger. In a preferred embodiment of the cam actuator mechanism, a firing cam is secured to the firing cable and slidably mounted on one of the jaws by one or more guide pins formed thereon which are slidably received in inclined cam slots formed on the jaw. A cam actuator surface on the firing cam engages a cam follower surface on the staple driver. The staple driver is advanced by movement of the guide pins in the inclined cam slots and by relative movement of the cam actuator surface along the cam follower surface when the firing cam is actuated by the firing cable.

The cam actuator mechanism has a compact construction which enables the stapling head assembly to be reduced in size in comparison with the prior art. This compact construction allows the stapling head assembly to be positioned more easily at restricted surgical sites, e.g., in the pelvic area.

A further aspect of the invention relates to an improved actuator mechanism comprising a jaw closure lever for closing the jaws of the surgical instrument to move the anvil into a tissue clamping position and a staple firing trigger for actuating the staple driver. The jaw closure lever is pivotally mounted on the actuator assembly for movement from an open position to a closed position to close the jaws and the staple firing trigger is pivotally mounted on the jaw closure lever. A deployment mechanism is provided for deploying the staple firing trigger in an inoperative position with the jaw closure lever in its open position and in a firing position when said jaw closure lever is moved from its open position to its closed position. The staple firing trigger is actuatable from its firing position to actuate the staple driver. The deployment means prevents actuation of the staple firing trigger until the jaw closure lever is moved to its closed position and permits actuation of the staple firing trigger after the jaw closure lever is moved to its closed position. Preferably, the stapling instrument includes means for locking the firing trigger to the jaw closure lever after actuation of the firing trigger to provide a visual indication that the stapling instrument has been fired.

A preferred embodiment of the surgical instrument comprises a linear stapling instrument for applying one or more surgical staples to the tissue. Preferably, the stapling instrument has a stapling head assembly including a fixed jaw which supports a staple holder adapted to receive a plurality of surgical staples arranged in one or more rows and a movable jaw which supports an anvil for clamping the tissue against the staple holder when the jaws are closed. Jaw coupling means is provided for slidably and pivotally coupling the movable jaw to the fixed jaw. The jaw coupling means includes a slidable roller pin slidably and rotatably mounted in guide slots formed in each of the jaws.

BRIEF DESCRIPTION OF THE DRAWINGS

The foregoing and other objects, aspects and advantages will be better understood from the following detailed description of the preferred embodiments of the invention with reference to the drawings, in which:

FIG. 1 is a perspective view of a surgical stapling instrument constructed in accordance with this invention which includes a support shaft with a flexible section for mounting a stapling head assembly on an actuator handle assembly;

FIG. 2 is a side elevation of the surgical stapling instrument of FIG. 1;

FIG. 3 is a partially cutaway side view of the surgical stapling instrument of FIG. 2 in a bent configuration to adjust the orientation of the stapling head assembly;

FIG. 4 is an enlarged, partially cutaway side view showing the flexible section of the support shaft of the surgical stapling instrument of FIG. 2;

FIG. 5 is an enlarged partially cutaway side elevation showing an alternative embodiment of the flexible section of the support shaft;

FIG. 6 is a partially cutaway side elevation showing an actuator mechanism contained within the actuator handle assembly of FIG. 2;

FIG. 7 is a partially cutaway side elevation showing a set of cam slots formed in the stapling head assembly of FIG. 2;

FIG. 8 is a partially cutaway side elevation showing a control linkage of the actuator mechanism of FIG. 6;

FIG. 9 is a partially cutaway side elevation showing a tissue retaining pin and a placement arm within the stapling head assembly of FIG. 2;

FIG. 10 is a partially cutaway side elevation showing a stapling firing trigger of the actuator mechanism of FIG. 6;

FIG. 11 is an enlarged longitudinal section showing a sliding cam mechanism within the stapling head assembly of FIG. 2;

FIG. 12 is an enlarged longitudinal section showing a portion of the flexible support shaft of FIG. 5 in a straight condition;

FIG. 13 is an enlarged longitudinal section showing a portion of the flexible support shaft of FIG. 5 in a bent condition;

FIG. 14 is an exploded perspective view of the actuator mechanism of FIG. 6;

FIG. 15 is a partially cutaway side view showing the operation of the actuator mechanism of FIG. 6;

FIG. 16 is a partially cutaway side view showing the stapling head assembly of FIG. 2 in a partially closed position;

FIG. 17 is a partially cutaway side view showing the stapling head assembly of FIG. 2 in a fully closed position.

FIG. 18 is an exploded perspective view showing the components of the stapling head assembly;

FIG. 19 is an enlarged, partially cutaway proximal end view of the movable jaw which supports the anvil of the stapling head assembly;

FIG. 20 is an enlarged, partially cutaway distal end view of the fixed jaw which supports the staple cartridge of the stapling head assembly;

FIG. 21 is an enlarged, partially cutaway top view of the stapling head assembly;

FIG. 22 is an enlarged, fragmentary section view of the stapling head assembly along line 22—22 of FIG. 16;

FIG. 25 is an enlarged front or distal end view of the staple driver of the stapling head assembly;

FIG. 26 is a side view of the staple driver of FIG. 25;

FIG. 27 is a longitudinal section of the staple driver along line 27—27 of FIG. 25;

FIG. 28 is a longitudinal section of the staple driver along line 28—28 of FIG. 26;

FIG. 29 is a side view of a metal insert for the staple driver of FIGS. 25–28;

FIG. 32 is an enlarged, partially cutaway vertical section showing a first row of staples in the stapling head assembly with the jaws open to receive a tissue lumen therebetween;

FIG. 33 is an enlarged, partially cutaway vertical section showing a second row of staples in the stapling head assembly with the jaws partially closed to capture the tissue lumen therebetween;

FIG. 34 is an enlarged, partially cutaway vertical section of the stapling head assembly with the jaws closed and the staples advanced through the tissue lumen into contact with the anvil;

FIG. 35 is an enlarged, partially cutaway vertical section of the stapling head assembly with the jaws closed and the staples driven against the anvil and formed into a B-shaped configuration;

FIG. 36 is an enlarged vertical section of a knuckle housing which provides a pivot connection for the stapling head assembly;

FIG. 37 is a bottom view of the knuckle housing of FIG. 36;

FIG. 38 is an enlarged front view of a knuckle pin pivotally supported by the knuckle housing of FIG. 36;

FIG. 39 is a side view of the knuckle pin of FIG. 38;

FIG. 40 is a rear view of the knuckle pin of FIG. 38;

FIG. 41 is an enlarged partially cutaway top view of the knuckle pin of FIG. 39;

FIG. 42 is an enlarged partially cutaway section view of the knuckle pin along line 42—42 of FIG. 39;

DETAILED DESCRIPTION OF PREFERRED EMBODIMENTS

Figure 23:
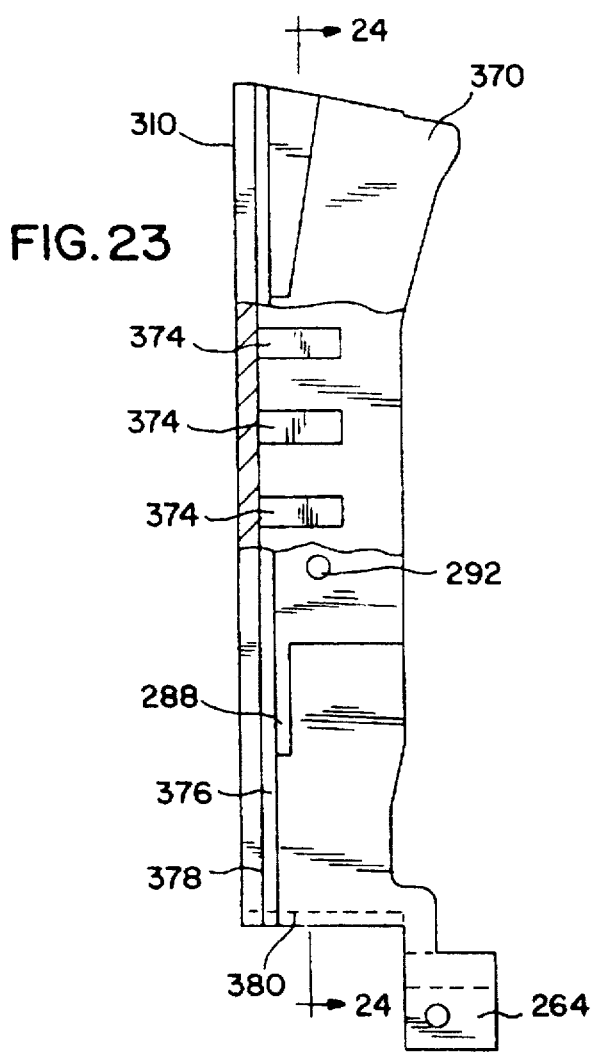
FIG. 23 is an enlarged, partially cutaway side view of the staple cartridge of the stapling head assembly.

Referring to FIG. 1, the present invention is embodied in a surgical stapling instrument, generally 50, which includes a distal stapling head assembly 60 connected by a support shaft assembly 70 to a proximal actuator handle assembly 80. The stapling head assembly 60 includes a proximal or fixed jaw 62 which supports a staple cartridge 64 and a distal or movable jaw 66 which supports a staple forming anvil 68 (FIG. 2). The staple cartridge 64 receives one or more rows of staples 65 (FIG. 28) which are driven against the anvil 68 and formed into a B-shaped configuration to fasten tissue together. For example, nineteen staples are held in the staple cartridge 64 and arranged in two staggered rows. It will be understood by persons skilled in the art that the surgical stapling instrument 50 can be adapted to operate with two-part surgical fasteners instead of the staples 65.

As shown in FIG. 1, the proximal or fixed jaw 62 is mounted in a hinge-like fashion on a pivot connection 72 which permits the stapling head assembly 60 to pivot about a vertical axis 52 into different angular orientations relative to a centerline or longitudinal axis 54 of the support shaft assembly 70. For example, the pivot connection 72 is arranged to allow the stapling head assembly 60 to pivot about the vertical axis 52 in approximately 20° increments. The articulated stapling head assembly 60 is pivotable either clockwise or counterclockwise about the vertical axis 52 to positions oriented at about ±20°, ±40°, ±60° and ±80° relative to the longitudinal axis or centerline 54. The support shaft assembly 70 is rotatably mounted on the actuator handle assembly 80 for rotation about the longitudinal axis or centerline 54. Preferably, the support shaft assembly 70 is rotatable over an angular range of approximately 340° or more about the centerline 54. A control knob 82 is rotatably mounted at the distal end of the actuator handle assembly 80 to allow the support shaft assembly 70 to be unlocked for rotation and to be locked in any desired rotational orientation.

The shaft assembly 70 includes a tubular support shaft 74 rotatably mounted on the actuator handle assembly 80 and secured by a coupling sleeve 75 to a flexible tubular shaft 76. The flexible tubular shaft 76 is capable of bending in any radial direction relative to the centerline 54 of the shaft assembly 70 into a bent or curved shape (FIG. 3). The hinge-like pivot connection 72 is mounted on a coupling sleeve 78 at the distal end of the flexible shaft 76. The tubular support shaft 74, the central coupling sleeve 75, and the distal coupling sleeve 78 can be made of metal, e.g., aluminum.

The actuator handle assembly 80 includes a pivotally mounted closure lever 84 for closing the movable jaw 66 toward the fixed jaw 62 to clamp a tubular section of tissue between the jaws 62 and 66. The actuator handle assembly 80 also includes a pivotally mounted firing trigger 86 for actuating the stapling head assembly 60 to drive the staples from the staple cartridge 64 through the tissue and to form the staples against the anvil 68. A firing safety lever 88 is pivotally mounted on the closure lever 84. With the firing safety lever 88 in its latched position (FIG. 2), the staple firing trigger 86 is locked against movement relative to the closure lever 84 to prevent the firing of the staples in the staple cartridge 64.

As shown in FIG. 1, the actuator handle assembly 80 includes a pair of hollow handle sections 90 and 92 made of plastic material and adapted to snap fit together at snap connector 94. Each of the handle sections 90 and 92 includes a depending handle grip 96. The depending handle grips 96 provide a hollow channel 98 therebetween for receiving the closure lever 84 when it is actuated to close the stapling head assembly 60.

Figure 30:
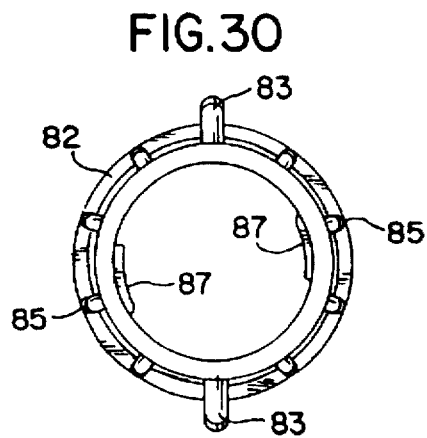
FIG. 30 is an enlarged front view of a control knob mounted at the distal end of the actuator handle assembly.
Figure 31:
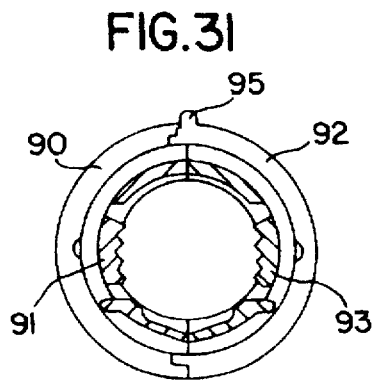
FIG. 31 is an enlarged vertical section along line 31—31 of FIG. 8 showing a pair of locking fingers on the actuator handle assembly actuated by the control knob.

Referring to FIGS. 1 and 30, the control knob 82 has two radially projecting longitudinal fins 83 at diametrically opposed positions and a series of longitudinal ribs 85 uniformly spaced about its circumference. The fins 83 and ribs 85 act as finger grips to facilitate the manual rotation of the control knob 82 by the surgeon. The control knob 82 is mounted for rotation over a range of approximately 90° about the longitudinal axis 54 of the support shaft assembly 70. A pair of cams 87 (FIG. 30) is located at diametrically opposed positions inside the control knob 82. The cams 87 are arranged to actuate a pair of resilient locking fingers 91 and 93 (FIG. 31) on the handle sections 90 and 92, respectively. The locking fingers 91 and 93 include a series of serrations or teeth 97 and 99, respectively, which are adapted to engage a set of circumferential teeth 77 on the outside of the tubular shaft 74. With the control knob 82 rotated to its locked position, the flexible locking fingers 91 and 93 are engaged by the cams 87 and are retained in engagement with the circumferential teeth 77 to lock the tubular shaft 74 against rotation. When the control knob 82 is rotated to its unlocked position, the cams 87 are disengaged from the locking fingers 91 and 93 which can be deflected away from the circumferential teeth 77 when the tubular shaft 74 is rotated relative to the actuator handle assembly 80.

In the preferred embodiment, the rotation of the shaft assembly 70 is constrained to the range of about ±170 degrees by a raised tab 79 (FIG. 6) on the tubular shaft 74 which is engageable with an end stop (not shown) on each of the handle sections 90 and 92 to limit the amount of rotation. The circumferential teeth 77 on the tubular shaft 74 and the locking fingers 91 and 93 provide a detent mechanism which defines twenty-two angular positions for rotation of the shaft assembly 70.

A longitudinal indicator flange 95 (FIG. 1) is formed at the top of the handle section 92 adjacent to the control knob 82. In the locked position, one of the fins 83 on the control knob 82 is aligned with the flange 95 to indicate that the tubular shaft 74 is locked against rotation. In the unlocked position, the fins 83 on the control knob 82 are rotated to a position about 90° from the flange 95 to indicate that the tubular shaft 74 is free to rotate.

Referring to FIGS. 1 and 14, the actuator handle assembly 80 includes an actuator mechanism, generally 100, contained within the hollow plastic handle sections 90 and 92. Preferably, the components of the actuator mechanism 100 consist of a rigid material, for example, a metal such as stainless steel. The actuator mechanism 100 includes a pair of outer chassis plates 102 which are similar in shape to the handle sections 90 and 92. Each of the handle sections 90 and 92 is provided with a set of internal flanges and ribs which support the chassis plates 102 in a fixed position within the actuator handle assembly 80 when the handle sections 90 and 92 are snap fit together. The chassis plates 102 are fastened together in a spaced parallel relationship by a pair of transverse connecting pins 104 located adjacent to the distal ends of the chassis plates 102 and by a pair of connecting pins 106 extending transversely between a pair of depending grip portions 108 of the chassis plates 102. An upper connecting pin 110 joins the top distal portions of the chassis plates 102 together and pivotally supports the other components of the actuator mechanism 100. A pair of opposed, hollow semi-cylindrical flanges 112 extend axially from the distal ends of the chassis plates 102 for receiving the tubular support shaft 74 therebetween.

The actuator mechanism 100 includes a pair of closure lever plates 114 each including a pivot hole 116 for receiving the connecting pin 110 to pivotally support the closure lever plates 114 for pivotal movement relative to the chassis plates 102. The closure lever plates 114 are secured together in a spaced parallel relationship by a transverse connecting pin 118 which rotatably supports a pulley 120. The closure lever plates 114 include elongated depending lever portions 122 which are contained inside a hollow plastic closure lever shroud 124 (FIG. 6) to provide the jaw closure lever 84 of the actuator handle assembly 80.

As shown in FIG. 14, a firing trigger plate 126 is pivotally mounted between the closure lever plates 114 by a pair of transverse pivot pins 128 (one shown) extending from its opposite sides and rotatably received in a pair of pivot holes 130 (one shown) formed in the closure lever plates 114. The firing trigger plate 126 is mounted within a hollow plastic firing trigger shroud 132 (FIG. 6) to provide the staple firing trigger 86 of the actuator handle assembly 80. The firing trigger plate 126 has an enlarged proximal end portion 134 provided with a pair of firing lever deployment pins 136 extending transversely from its opposite sides and slidably received in a pair of arc-shaped slots 138 (one shown) formed in the closure lever plates 114. The outer ends of the firing lever deployment pins 136 extend through the slots 138 into a pair of firing lever deployment cam slots 140 formed in the chassis plates 102. A finger 142 on the enlarged proximal portion 134 of the trigger firing plate 126 defines an anchor hole 144 for receiving an anchor 146 secured to the proximal end of a firing cable 148 (FIG. 10). Initially, the cable 148 extends loosely around the pulley 120 and over the pivot pin 110. The cable 148 passes under the upper connecting pin 104 and through a vertical slot 150 formed in a stop plate 151 located on the distal side of the connecting pins 104. The stop plate 151 includes a pair of tabs 152 projecting laterally from its opposite sides and received in a pair of mounting holes 153 formed in the chassis plates 102. When the staple firing trigger 86 is actuated, the slack in the cable 148 is taken up by the enlarged proximal end portion 134 of the trigger firing plate 126.

The actuator mechanism 100 includes a closure control linkage, generally 154, comprising a link 155 and a fork plate 156 pivotally connected together by a pair of transverse pivot pins 158 extending in opposite directions from the lower end of the link 155. The outer ends of the pivot pins 158 extend into a pair of Z-shaped guide slots 160 (one shown) formed in the chassis plates 102. Each of the guide slots 160 includes an upper distal section 161 and a lower proximal section 162 which overlap and define a detent or shoulder 159 in the guide slot 160. A pair of transverse pivot pins 163 (one shown) at the upper end of the link 155 extend transversely in opposite directions from the link 155. The pivot pins 163 are received in a pair of pivot holes 164 formed in a pair of depending distal fingers 165 on the closure lever plates 114. Each finger 165 is inclined downwardly and forwardly to define an inverted V-shaped notch 166 behind the finger 165. A closure cable 170 extends through a slot 167 at the front of the closure fork plate 156. The proximal end of the closure cable 170 is secured to an anchor 168 which is inserted through an assembly hole 169 at the proximal end of the slot 167 and engages the inside of the fork plate 156. The closure control linkage 154 applies tension to the closure cable 170 when the closure lever plates 114 are actuated by the closure control lever 84. The closure cable 170 extends over the lower coupling pin 104 and through the vertical slot 150 formed in the stop plate 151.

Referring to FIGS. 2 and 4, the flexible tubular support shaft 76 comprises a dual helical coil structure comprising a first elongated helical member 172 and a second elongated helical member 174 which are concentrically wound together with the coils 176 of the first helical member 172 alternately interspersed with the coils 178 of the second helical member 174. As shown in FIG. 4, each coil 176 of the helical member 172 has a round cross section. Each coil 178 of the helical member 174 has a triangular, wedge-shaped cross section defining a pair of inwardly sloped surfaces 180 which engage the round exterior surfaces of the adjacent round coils 176. The wedge-shaped coils 178 are positioned between the round coils 176 to maintain a desired separation between the adjacent round coils 176 and to maintain the first helical member 172 in tension. Each of the triangular coils 178 has a rounded outer surface to prevent the trapping of surgical gloves during use of the surgical stapling instrument 50. The helical coil members 172 and 174, which are preferably made of stainless steel, allow the flexible shaft 76 to be bent in any radial direction relative to the longitudinal axis or centerline 54 of the support shaft assembly 70. Inside the helical coil members 172 and 174 is a concentrically mounted cable support tube 182, preferably made of a malleable metal such as aluminum, which allows the flexible 76 to assume its bent or curved shape. The cable support tube 182 is flexible in any radial direction relative to the longitudinal axis or centerline 54 of the support shaft assembly 70. The cable support tube 182 enables the flexible support shaft 76 to assume its curved configuration and to resist tension from the cables 148 and 170 when the stapling head assembly 60 is actuated.

In the preferred embodiment, the flexible support shaft 76 is adapted to be bent within a predetermined range, e.g., up to about ±30° in any direction from its straight configuration. After bending, the flexible support shaft 76 maintains its bent shape until further manipulated. The malleable cable support tube 182 prevents the bent support shaft 176 from inadvertently straightening. This shape retention feature permits access of the stapling head assembly 60 into the pelvic cavity while avoiding contact of the actuator handle assembly 80 with the viscera or body wall. The helical coil members 172 and 174 provide a geometry such that the axis of the shaft assembly 70 remains a substantially constant length during the bending of the flexible support shaft 76. This feature avoids any undesirable change in length which would result in motion of the taut cable system. The twin helical coil construction also provides a solid load path which resists the compressive forces during closure and firing while avoiding any tendency for the flexible support shaft 76 to return to the straight condition.

In addition, the geometry of the circular coils 176 and the triangular coils 178 is such that, at a bending angle of about 30°, one or the other of the coils becomes solid, i.e., either the adjacent round coils 176 engage each other or the adjacent triangular coils 178 engage each other. This condition causes a sharp increase in the force required to bend the flexible support shaft 76 and provides a limit on the extent of the bending motion. This limitation on the angle of bend keeps the cable friction forces low so that the system operates in the regime of substantially constant axis length. The malleable cable support tube 182 is free to slide axially within the helical members 172 and 174 so that any change in the length of the cable support tube 182 due to plastic deformation does not effect the force required to bend the flexible support shaft 76.

Referring to FIG. 5, in an alternative embodiment of the flexible support shaft 76, the wedge-shaped coils 178 are reduced in width compared with the diameter of the round coils 176. Also, the wedge-shaped coils 178 are shaped to allow the adjacent round coils 176 on the inside of the bend to engage each other when the flexible support shaft 76 is bent to about a 30° bending angle. The helical coil spring member 172 and the helical wrap wire member 174 are coiled together along a common longitudinal axis 175 with the round coils 176 alternating with the triangular or wedge-shaped coils 178 and the coil spring member 172 in tension. The wrap wire member 174 is wrapped about the coil spring member 172 with the wedge-shaped coils 178 positioned between the round coils 176 to maintain a desired separation between the adjacent round coils 176 when the support shaft assembly 76 is straight. The wedge-shaped coils 178 are forced between the adjacent round coils 176 to maintain the coil spring member 172 in tension. The details of the flexible support shaft 76, the coil spring member 172, the wrap wire member 174, the round coils 176 and the wedge-shaped coils 178 are described in a co-pending U.S. patent application entitled "Flexible Support Shaft Assembly", filed on the same date and assigned to the same assignee, Ethicon, Inc., as the present application, and herein incorporated by reference.

As shown in FIG. 12, each of the wedge-shaped coils 178 initially separates the adjacent round coils 176 longitudinally from each other when the flexible support shaft 76 is straight. The round coils 176 and the wedge-shaped coils 178 are aligned along the common longitudinal axis 175. The wedge-shaped coils 178 are slidable relative to the round coils 176 to allow the flexible support shaft 76 to bend in a transverse direction relative to its longitudinal axis 175. The sliding action of the wedge-shaped coils 178 allows the flexible support shaft 76 to bend until the round coils 176 on the inside of the bend engage each other and limit the bending of the flexible support shaft 76.

Referring to FIG. 13, as the flexible support shaft 76 is bent transversely relative to its longitudinal axis 175, the wedge-shaped coils 178 are shifted laterally relative to the adjacent round coils 176. Also, the longitudinal axis 179 of the wedge-shaped coils 178 is shifted slightly relative to the longitudinal axis 175 of the round coils 176 in the direction of the bending of the flexible support shaft 76. The portions of the round coils 176 on the inside of the bend move closer together while the portions of the round coils 176 on the outside of the bend move farther apart. As a result of the sliding action of the wedge-shaped coils 178 relative to the round coils 176, the flexible support shaft 76 is bent into a curved configuration. The bending of the flexible support shaft 76 occurs without any substantial change in the overall length of the flexible support shaft assembly 76 and without stretching of the coil spring member 172 along its axis 175 until the round coils 176 on the inside of the bend move into engagement with each other. Up to this point, the bending of the flexible support shaft 76 can be accomplished by applying a relatively small bending force to the coil spring member 172 and the wrap wire member 174.

After the round coils 176 on the inside of the bend engage each other, a substantially increased bending force must be applied to obtain any further bending of the flexible support shaft 76 in the same direction. Because the portions of the round coils 176 on the inside of the bend are in contact with each other, any additional bending of the flexible support shaft 76 requires the stretching of the coil spring member 172 to move the portions of the round coils 176 on the outside of the bend farther apart. Thus, the point at which the round coils 176 on the inside of the bend move into engagement with each other defines a limit on the bending of the support shaft 76 in the transverse direction.

Referring to FIG. 5, the dual coil structure of the flexible support shaft assembly 76 with the clamping sleeves 184 is assembled in the following manner. The wrap wire member 174 is wrapped about the coil spring member 172 to position the wedge-shaped coils 178 between the adjacent round coils 176 with the coil spring member 172 in tension. A series of clamping sleeves 184 made of compressible metal, e.g., aluminum, is positioned at uniformly spaced locations along the coiled helical members 172 and 174. Preferably, the clamping sleeves 184 are spaced apart by intervals of approximately three inches. Each of the clamping sleeves 184 is compressed or swaged mechanically to clamp the helical members 172 and 174 together. Then, the helical members 172 and 174 are divided into a plurality of flexible support shaft sections 76 of uniform length by cutting the helical members 172 and 174 at the mid-points of the clamping sleeves 184. Each of the resulting flexible tubular shaft sections 76 is clamped at its opposite ends by the clamping sleeves 184 to maintain the tension in the coil spring member 102 and prevent the unraveling of the coiled helical members 172 and 174.

Figure 48:
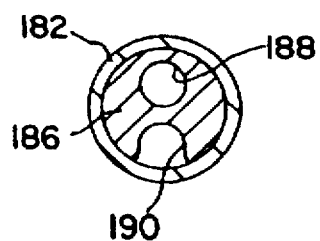
FIG. 48 is an enlarged fragmentary section of the support shaft along line 48—48 of FIG. 4.

Referring to FIG. 4, a double lumen cable support member 186 is mounted inside the cable support tube 182. The cable support member 186 has an elongated cylindrical configuration and extends from the distal end of the flexible support shaft 76 through the coupling sleeve 75 to a point adjacent to the proximal end of the tubular support shaft 74. The cable support member 186 includes separate longitudinal passages 188 and 190 (FIG. 48) for receiving the firing cable 148 and the closure cable 170, respectively.

The coupling sleeve 75 has an intermediate cylindrical wall 192 provided with a central axial opening 194 for receiving the proximal end of the cable support tube 182. The clamping sleeve 184 at the proximal end of the flexible support shaft 76 is received and secured in a hollow cylindrical section 196 of the coupling sleeve 75. The distal end of the tubular support shaft 74 is received in a hollow cylindrical proximal section 198 of the coupling sleeve 75. The distal end of the tubular support shaft 74 has a series of annular grooves 200 of reduced diameter which provide a series of longitudinally spaced annular ridges 202. The proximal section 198 of the coupling sleeve 75 is deformed, e.g., by magneforming, into contact with the annular grooves 200 and annular ridges 202 to secure the coupling sleeve 75 to the tubular support shaft 74.

Referring to FIG. 9, the pivot connection 72 which pivotally mounts the stapling head assembly 60 on the shaft assembly 70 comprises a knuckle housing 210 which is mounted on the flexible tubular support shaft 76 by the coupling sleeve 78. The clamping sleeve 184 at the distal end of the flexible support shaft 76 is received in the distal coupling sleeve 78 which is secured, e.g., by magneforming, to the clamping sleeve 84. The knuckle housing 210 includes a pair of hollow, cylindrically shaped hinge arms 212 and 214 which receive a cylindrical knuckle pin 216 for rotation in a hinge-like fashion. A distally projecting flange 218 (FIG. 11) is formed at the bottom of the knuckle pin 216. A passage 220 extends radially through the knuckle pin 216 for slidably receiving the closure cable 170. The knuckle housing 210 and the knuckle pin 216 are preferably made of plastic material. The knuckle housing 210 is insert molded onto an annular flange 79 projecting distally from the coupling sleeve 78 which is preferably made of aluminum.

The fixed jaw 62 includes a head plate 222, preferably made of metal, e.g., stainless steel, which is adapted to receive and support the staple cartridge 64. The head plate 222 is formed as a double-walled, inverted channel-shaped member with a pair of opposed vertical side walls 224 which are mirror images of each other. The staple cartridge 64, preferably made of plastic material, has a narrow rectangular configuration and is mounted at the front of the head plate 222 between the side walls 224.

As shown in FIG. 7, the head plate 222 is pivotally supported by the knuckle housing 210 and the knuckle pin 216. The side walls 224 include an upper pair of flanges 226 which are curved inwardly toward each other and are slidably received in an arcuate channel 228 (FIG. 11) formed at the top of the knuckle housing 210. The side walls 224 also include a lower pair of flanges 230 which are curved inwardly toward each other and are rotatably received behind the knuckle pin 216 between the hinge arms 212 and 214. With the knuckle pin 216 inserted into the cylindrical flanges 212 and 214, the head plate 222 is attached to the knuckle housing 210 in a hinge-like manner to pivotally support the stapling head assembly 60 at the distal end of the support shaft assembly 70. The side walls 224 of the head plate 222 include a pair of distally projecting side plates 232 which are spaced apart and secured together by a bearing pin 234. The lower flange 218 on the knuckle pin 216 is received between the side plates 232.

Figure 43:
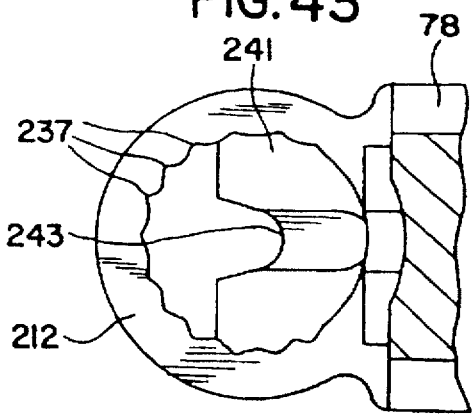
FIG. 43 is an enlarged, partially cutaway section view of the knuckle housing along line 43—43 of FIG. 36.
Figure 44:
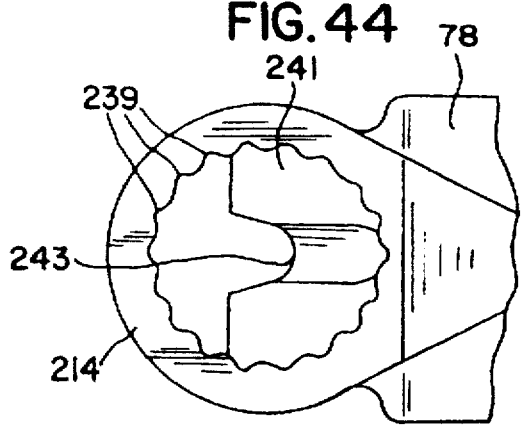
FIG. 44 is an enlarged, partially cutaway bottom view of the knuckle housing of FIG. 36.

Referring to FIGS. 36 and 38, the knuckle pin 216 has a set of detents 236 at its upper end which cooperate with a series of circumferentially spaced notches 237 on the interior of the upper hinge arm 212 to provide a first detent mechanism for controlling the pivotal movement of the knuckle pin 216 relative to the knuckle housing 210. The knuckle pin 216 also includes a set of detents 238 at its lower end which cooperate with a series of circumferentially spaced notches 239 formed on the interior of the lower hinge arm 214 to provide a second detent mechanism for controlling the pivotal movement of the knuckle pin 216 relative to the knuckle housing 210. As shown in FIG. 41, there are three detents 236 at the top of the knuckle pin 216 which are spaced 40° apart. The three detents 236 cooperate with thirteen notches 237 (FIG. 43) which are uniformly spaced apart by 20° on the inside of the upper hinge arm 212. As shown in FIG. 42, there are six detents 238 at the bottom of the knuckle pin 216 which are uniformly spaced 60° apart. The six detents 238 cooperate with eighteen notches 239 (FIG. 44) which are uniformly spaced apart by 20° on the inside of the lower hinge arm 214. The upper and lower detents 236 and 238 on the knuckle pin 216 engage the notches 237 and 239 on the interior of the upper and lower hinge arms 212 and 214, respectively, to define 20° intervals for the pivotal movement of the stapling head assembly 60 about the vertical axis 52. The upper detents 236 and notches 237 allow the stapling head assembly 60 to pivot over a range of about ±80° relative to the longitudinal axis 54.

As shown in FIG. 36, the knuckle housing 210 has an upper flange 241 provided with an upwardly curved cable passage 243 for receiving the firing cable 148. The curved passage 243 in the knuckle housing 210 allows the firing cable 148 to turn smoothly at right angles as it passes through the knuckle housing 210. The top of the knuckle pin 216 has a beveled surface 245 (FIG. 39) which extends circumferentially over a range of about 200°. The beveled surface 245 provides a clearance for the firing cable 148 and allows the knuckle pin 216 to rotate about its axis without interference with the firing cable 148.

Figure 45:
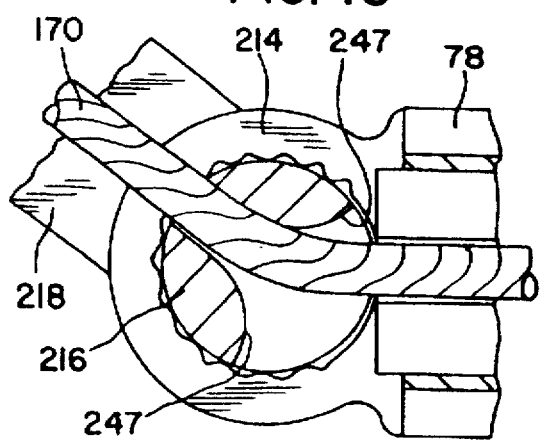
FIG. 45 is an enlarged, partially cutaway section view of the pivot connection showing the knuckle pin pivoted in the knuckle housing.

Referring to FIGS. 38–40, the cable passage 220 in the knuckle pin 216 is circular in shape for receiving the closure cable 170. The cable passage 220 has opposite inner walls 247 (FIG. 42) which curve outwardly in the proximal direction so that the cable passage 220 terminates at a rearwardly facing slot 249 (FIGS. 39–40) on the proximal side of the knuckle pin 216. As shown in FIG. 45, the oppositely curved walls 247 of the passage 220 provide a path of substantially constant length for the closure cable 170 as the knuckle pin 216 is rotated relative to the knuckle housing 210. This constant length feature tends to prevent changes in the tension on the closure cable 170 and changes in the gap between the staple cartridge 64 and the anvil 68 when the stapling head assembly 60 is rotated about the vertical axis 52 relative to the support shaft 70.

Referring to FIG. 9, the movable jaw 66 comprises a pair of generally L-shaped jaw plates 240, preferably made of metal, e.g., stainless steel, each including a front arm 242 projecting upwardly from a base member 244. A cam actuator finger 246 projects upwardly at the rear of each base member 244. The front arms 242 are secured together by a set of flush mount rivets 248 and are spaced apart by a hollow, generally L-shaped pilot member 250 (FIG. 11), preferably made of plastic. An insert member 251 of rigid material, preferably a metal such as stainless steel, is mounted inside the pilot member 250 and connected to the front arms 242 by the rivets 248. The metal insert 251 provides back-up stiffness for the plastic pilot member 250. The base members 244 of the movable jaw plates 240 are secured together by a transverse connecting pin 252. The staple forming anvil 68 has a pair of side flanges 69 (FIG. 21) which receive the pilot member 250 and the metal insert 251 therebetween. The L-shaped jaw plates 240 are secured to the side flanges 69 of the anvil 68 and to the pilot member 250 and the insert member 251 by the flush mount rivets 248. The anvil 68 is offset slightly in the proximal direction from the arms 242 to allow the elongated proximal edges 253 of the arms 242 to serve as cutting guides for a surgical knife or scalpel.

As shown in FIG. 7, the movable jaw 66 is slidably and pivotally mounted on the fixed jaw 62 in the following manner. The movable jaw plates 240 are slidably and pivotally connected to the head plate 222 by a roller or pivot pin 254 which is slidably and rotatably mounted in a pair of elongated slots 256 formed in the side plates 232. The outer ends 255 (FIG. 22) of the slidable roller or pivot pin 254 are reduced in diameter and are slidably received in a pair of elongated slots 258 formed in the base members 244 of the movable jaw plates 240. The roller or pivot pin 254 is both slidable and rotatable within the slots 256 and 258 to provide a sliding and rolling pivot connection between the side plates 232 and the base members 244 which reduces friction and allows the movable jaw 66 to slide and pivot into a closed position relative to the fixed jaw 62. The outer ends 235 of the bearing pin 234 are reduced in diameter and are slidably received in a pair of guide slots 260 formed adjacent to the distal ends of the base members 244. Each guide slot 260 includes a longitudinal section 261 and an upwardly inclined section 262. The bearing pin 234 and the guide slots 260 serve to guide the movable jaw 66 into an upright position parallel to the fixed jaw 62 when the stapling head assembly 60 is closed.

As shown in FIG. 11, the closure cable 170 extends through the knuckle housing 210 and the knuckle pin 216 and through a lower flange 264 on the staple cartridge 64 into a hollow spring housing 266 projecting laterally from the base of the pilot member 250. The closure cable 170 extends through a depending flange 268 on the pilot insert 251 and is anchored in an opening 270 at the front of the pilot member 250 by an anchor 272 secured to the distal end of the closure cable 170 and engaged with the depending flange 268. A compression return spring 274 extends between the depending flanges 264 and 268 to normally bias the movable jaw 66 to the open position. The closure cable 170 extends through the return spring 274.

At the top of the movable jaw 66, a passage 276 extends longitudinally through the tip of the pilot member 250. A tissue retaining pin 280 mounted on the fixed jaw 62 is received in the passage 276 when the movable jaw 66 is closed. The retaining pin 280 comprises an elongated resilient wire spring which is bent into a narrow U-shaped retainer tip 282 (FIG. 18) flanked by cantilever spring arms 284 which span the staple cartridge 64. The spring arms 284 terminate in base portions 286 which are inserted into a pair of slots 288 formed on opposite sides of the staple cartridge 64.

A pin placement arm 290 is pivotally mounted by a laterally projecting pivot pin 292 on each side of the staple cartridge 64. The pin placement arms 290 are positioned to engage the cantilever spring arms 284 of the tissue retaining pin 280. Each pin placement arm 290 includes a wedge-shaped cam 294 which projects laterally outward from a window 296 formed in each of the side walls 224 of the head plate 222. When the movable jaw 66 is closed, the cam actuator fingers 246 engage the cams 294 to pivot the pin placement arm 290 counterclockwise, as viewed in FIG. 9, to advance the tissue retaining pin 280 from the fixed jaw member 62 into the passage 276 formed in the pilot member 250. The tissue retaining pin 280 is also received in a notch 298 at the top of the anvil 68 to align the anvil 68 with the staple cartridge 64. When the movable jaw member 66 is opened, the cantilever spring arms 284 retract the tissue retaining pin 280 into the fixed jaw member 282. Also, the compression spring 274 (FIG. 11) returns the movable jaw member 66 to its open position.

As shown in FIG. 7, a plastic cover 300 is inserted between the vertical side walls 224 at the rear of the head plate 222. The cover 300 has a pair of forwardly projecting side flaps 302 (FIG. 2) which provide an earmuff-like shield over the cams 294 projecting through the windows 296 in the side walls 224. Each of the side flaps 302 includes an opening 304 for receiving a prong 306 (FIG. 7) projecting laterally from each of the side walls 224 to fasten the cover 300 on the head plate 222. A pair of fastener pins 310 projecting laterally from opposite sides at the top of the staple cartridge 64 are received in a pair of angled slots 312 formed in the side walls 224. The staple cartridge 64 is secured to the side walls 224 by a flush mount rivet 314 (FIG. 11) which extends transversely through the depending flange 264 at the bottom of the staple cartridge 64.

Referring to FIG. 11, a staple driver 320 is slidably mounted in the staple cartridge 64 for driving the staples 65 against the anvil 68. The staple driver 320 is preferably made of plastic material and, if desired, consists of a solid molded plastic unit. The staple driver 320 is actuated by a slidable firing cam 324 made of metal, e.g., stainless steel, which is slidably mounted on the fixed jaw 62 and secured to the distal end of the firing cable 148.

The firing cam 324 forms part of a dual cam actuator mechanism for actuating the staple driver 320 with different mechanical advantages when the staple firing trigger 86 is actuated. The dual cam actuator mechanism is adapted to actuate the staple driver 320 with a first mechanical advantage over a first portion of the stroke of the staple firing trigger 86 and with a second mechanical advantage over a second portion of the stroke of the staple firing trigger 86.

As shown in FIG. 7, the firing cam 324 includes a pair of laterally projecting pins 326 on each of its sides which are slidably received in a pair of inclined cam slots 328 formed in each of the side walls 224 of the head plate 222. The pins 326 and cam slots 328 provide a first portion of the dual cam mechanism for actuating the staple driver 320. Each cam slot 328 is inclined downwardly toward the front of the head plate 222, e.g., at an angle of 15° from the vertical axis 52 (FIG. 1). Each of the cam slots 328 terminates in a bottom vertical portion 330 oriented parallel to the vertical axis 52. As the firing cam 324 is pulled downwardly by the firing cable 148, the pins 326 ride along the inclined slots 328 so that the firing cam 324 and the staple driver 320 are displaced in the distal direction.

Referring to FIG. 11, the firing cam 324 is contoured at its distal edge to provide a pair of inclined cam actuator surfaces 332 which slidably engage a complementary pair of inclined cam follower surfaces 334 formed at the proximal edge of the staple driver 320. The cam actuator surfaces 332 and the cam follower surfaces 334 provide a second portion of the dual cam mechanism for actuating the staple driver 320. Preferably, both pairs of inclined cam surfaces 332 and 334 are inclined at an angle of 15° from the vertical axis 52. Each inclined cam actuator surface 332 on the firing cam 324 terminates in a flat cam surface 336 oriented parallel to the vertical axis 52. Similarly, each inclined cam follower surface 334 on the staple driver 320 terminates in a flat cam follower surface 338 oriented parallel to the vertical axis 52. As the firing cam 324 is pulled downwardly by the firing cable 148, the inclined cam surfaces 332 on the firing cam 324 ride along the inclined cam surfaces 334 on the staple driver 320 to push the staple driver 320 distally relative to the firing cam 324. The flat cam surfaces 336 on the firing cam 324 are arranged to engage the that cam surfaces 338 on the staple driver 320 before the pins 326 on the firing cam 324 arrive at the bottom vertical portions 330 of the inclined slots 328. When the firing cam 324 is actuated, the first cam mechanism provided by the inclined cam surfaces 332 and 334 bottoms out before the second cam mechanism provided by the pins 326 and inclined slots 328.

The dual cam mechanism of the stapling head assembly 60 occupies less space than the staple firing mechanisms of the prior art. Thus, the outer dimensions of the fixed jaw 62 which houses the dual cam mechanism are minimized to allow the stapling head assembly 60 to access restricted surgical sites, e.g., in the pelvic area.

Generally, the surgical stapling instrument 50 is operated in the following manner. With the jaws 62 and 66 open, the stapling head assembly 60 is articulated about the vertical axis 52 to a desired angular position relative to the longitudinal axis 54. The flexible tubular shaft 76 is bent into a curved configuration to conform to the anatomy of the patient. The control knob 82 is rotated to its unlocked position and the shaft assembly 70 is rotated about its longitudinal axis 54 to orient the actuator handle assembly 80 in a comfortable position for actuation by the surgeon. Then the control knob 82 is rotated to its locked position to lock the shaft assembly 70 against rotation relative to the actuator handle assembly 80.

Next, by manipulating the surgical stapling instrument 50 in a lever-like manner, the stapling head assembly 60 is positioned inside the body and a tissue lumen 55 (FIG. 32) to be stapled is located between the open stapler jaws 62 and 66. The movable jaw 66 is partially closed by actuating the jaw closure lever 84 with one hand. The tissue retaining pin 280 is advanced from the fixed jaw 62 into engagement with the movable jaw 66 to capture the lumen 55 (FIG. 33) between the jaws 62 and 66. The other hand is used to guide the stapling head assembly 60 into the desired position. With the jaw closure lever 84 in the intermediate or detent position, the stapling head assembly 60 can be moved along the captured lumen 55 to the desired stapling position. If desired, the jaw closure lever 84 can be returned to its inoperative position to return the movable jaw 66 to its fully open position and to retract the tissue retaining pin 280 into the fixed jaw 62 to allow the stapling instrument 50 to be withdrawn from the body cavity for adjustment of the articulation of the stapling head assembly 60 and the curvature of the flexible tubular shaft 76.

When the stapling head assembly 60 is located in the desired stapling position on the lumen 55, the jaw closure lever 84 is moved to its fully clamped position (FIG. 15) to completely close the jaw 66 to clamp the lumen 55 between the staple cartridge 64 and the anvil 68. Next, the firing safety lever 88 is released to enable the firing trigger 86 to be actuated. The firing trigger 86 is grasped and squeezed to fire the staples 65 in the staple cartridge 64. As shown in FIGS. 34 and 35, the staples 65 are advanced into engagement with the anvil 68 and are formed into a B-shaped configuration to staple the tissue lumen 55 together. The firing trigger lever 86 is locked to the jaw closure lever 84 once the staples 65 are fully fired. The lumen 55 is transected by using right angle scissors or by running a scalpel along the cutting guides formed at the longitudinal edges of the staple cartridge 64 or the anvil 68. The jaws 62 and 66 are unclamped from the lumen 55 by pushing the base of the closure lever 84 forward. With the jaws 62 and 64 unclamped and the tissue retaining pin 280 retracted, the stapling instrument 50 is removed from the body cavity.

Referring to FIGS. 1 and 14, during the closure of the stapling instrument 50 by actuation of the jaw closure lever 84, the forces applied by hand to the depending lever portions 122 of the closure lever plates 114 are transmitted by the fingers 165 and the closure control linkage 154 to the closure cable 170. The force applied to the closure cable 170 is transmitted via the cable anchor 272 to the depending flange 268 (FIG. 11) of the insert member 251 to pull the movable jaw 66 toward the fixed jaw 62. Initially, the movable jaw 66 is pivoted about the slidable roller pin 254 into an upright position (FIG. 16). The jaw plates 240 are guided in movement relative to the base members 232 by the roller pin 254 which slides and rotates in the slots 256 and 258 and by the bearing pin 234 and the inclined portions 262 of the guide slots 260.

As the movable jaw 66 is pivoted into the upright position, the cam fingers 246 engage the corresponding cams 294 and pivot the pin placement arms 290 counterclockwise, as viewed in FIG. 9, about the pivot pins 292. The pin placement arms 290 bend the cantilever spring arms 284 forward to extend the tip portion 282 of the tissue retaining pin 280 through the opening at the top of the staple cartridge 64 and into the notch 298 at the top of the anvil 68. At this point, as shown in FIG. 16, the bearing pin 234 is positioned at the juncture between the longitudinal portion 261 and the inclined portion 262 of the guide slot 260. Also, as shown by phantom lines in FIG. 15, each of the pins 158 moves along the upper section 161 of the corresponding Z-shaped guide slot 160 and drops into a detent position engaging the shoulder 159 in the lower section 162 of the guide slot 160. The compression return spring 274 (FIG. 11) is slightly compressed to exert a return force on the jaw closure cable 170 to hold the pins 158 in the detent position against the shoulders 159. The tip portion 282 of the tissue retaining pin 280 extends across the gap between the staple cartridge 64 and the anvil 68 to capture the lumen 55 therebetween. The tissue retaining pin 280 prevents the partially closed jaws 62 and 66 from slipping off the lumen 55 as the stapling head assembly 60 is moved along the captured lumen 55 to the desired stapling position.

After the movable jaw 66 is pivoted into the upright position, the bearing pin 234 is slidably received in the longitudinal portions 261 of the guide slots 260 to allow the jaw plates 240 to slide longitudinally relative to the fixed jaw 62. Next, as shown by solid lines in FIG. 15, the jaw closure lever 84 is moved to its fully closed position within the slot 98 between the depending handle grips 96 of the actuator handle assembly 80. The control linkage 154 is pulled rearwardly and the pins 158 travel rearwardly along the lower sections 162 of the Z-shaped guide slots 160. As the movable jaw 66 is pulled closer toward the fixed jaw 62, the tip of the anvil 68 moves into engagement with a tissue stop 340 at the top of the staple cartridge 64. Thereafter, the movable jaw 66 pivots slightly about the tissue stop 340 until the bearing pin 234 is engaged by the distal ends of the guide slots 260 (FIG. 17). This bottoming out point occurs before the jaw closure lever 84 reaches the end of its travel. As the jaw closure lever 84 completes its stroke, the high mechanical advantage of the over-center control linkage 154 stretches the closure cable 170 and applies a high force, approximately 200 pounds, to pre-load the stapling jaw assembly 60 into the closed position. This high pre-load force resists the staple forming forces encountered during the firing of the staples 65 in the staple cartridge 64.

During the motion of the jaw closure lever 84, the staple firing trigger 86 is deployed from a substantially horizontal inoperative position (FIG. 2) into a substantially vertical firing position (FIG. 15) so that the staple firing trigger 86 can be grasped by the surgeon for firing of the stapling instrument 50. The pivot axis for the staple firing trigger 86 is provided by the pivot pins 128 on the firing trigger plate 126 which are received in the pivot holes 130 formed in the closure lever plates 114. As the jaw closure lever 84 is drawn backward, the staple firing trigger 86 is carried backward with the jaw closure lever 84 and the deployment pins 136 travel along a fixed cam track defined by the cam slots 140 formed in the chassis plates 102. The cam slot 140 is shaped such that the staple firing trigger 86 remains substantially horizontal until the jaw closure lever 84 reaches the detent position, after approximately 20 percent of the closure travel.

Initially, as shown in FIG. 6, each of the deployment pins 136 moves downwardly and rearwardly along an inclined cam track section 350 of the corresponding cam slot 140. As shown by phantom lines in FIG. 15, when the jaw closure lever 84 arrives at the detent position, each pivot pin 158 drops downwardly into engagement with the shoulder 159 in the corresponding Z-shaped guide slot 160 and the deployment pin 136 arrives at the bottom of the inclined cam track section 350. When the jaw closure lever 84 is moved past the detent position, each pivot pin 158 is moved backward along the proximal section 162 of the Z-shaped guide slot 160 and each deployment pin 136 travels along a curved cam track section 352 which forces the staple firing trigger 86 to rotate about the pivot pins 128 to the substantially vertical firing position. As long as the deployment pin 136 is located in either the inclined cam track section 350 or the curved cam track section 352, the movement of the jaw closure lever 84 can be reversed to return the staple firing lever 86 to the substantially horizontal position.

During the deployment of the staple firing trigger 86, the motion of the trigger firing plate 126 relative to the closure plate 114 is restricted by the deployment pins 136 which are captured in the cam track sections 350 and 352. Thus, any manual pulling force applied to the staple firing trigger 86 during its deployment merely urges the jaw closure lever 84 toward its closed position. Since the deployment pins are captured in the cam track sections 350 and 352, the staple firing lever 86 cannot be actuated to fire the staples in the staple cartridge 64. When the jaw closure lever 84 is pulled to its fully closed position, the pivot pins 158 are located at the proximal ends of the Z-shaped guide slots 160 and each of the deployment pins 136 is located at a rear corner 354 of the corresponding cam slot 140 where the curved cam track sections 352 and 356 intersect. After the firing safety lever 88 is released, the staple firing trigger 86 is free to pivot relative to the jaw closure lever 84 to actuate the stapling head assembly 60.

Next, the staple firing trigger 86 is grasped and pulled toward the jaw closure lever 84. The staple firing plate 126 is pivoted about the pivot pins 128 in a counter-clockwise direction, as viewed in FIG. 10. The arc-shaped slots 138 in the jaw closure plates 114 are aligned with the curved cam track sections 356 of the cam slots 140 in the chassis plates 102. The deployment pins 136 are free to travel along the curved cam track sections 356 to allow the staple firing trigger 86 to pivot to its fully closed position to actuate the stapling head assembly 60. As the staple firing plate 126 is pivoted toward its fully closed position, the firing cable 148 is wrapped around the enlarged proximal end portion 134 to take up the slack in the firing cable 148. When the staple firing trigger 86 is moved to its fully actuated position, the firing cable 148 is pulled around the pulley 120 and placed in tension to actuate the firing cam 324 in the stapling head assembly 60. The firing of the staples in the staple cartridge 64 is explained in more detail below.

Once the stapling instrument 50 is fired, a pair of detents 360 (one shown in FIG. 6) on the interior of the firing trigger shroud 132 are snap-fit into a corresponding pair of apertures 362 in the closure lever shroud 124 to attach the stapling firing trigger 86 to the jaw closure lever 84. This snap feature cannot be reversed by the surgeon so that the staple firing trigger 86 remains attached to the jaw closure lever 84 indicating that the stapling instrument 50 has been fired. The stapling head assembly 60 is opened after firing by pushing on a contact pad 364 at the tip of the closure lever shroud. The jaw closure lever 84 and the stapling firing trigger 86 move together as a single unit into a substantially vertical open position. During this motion of the jaw closure lever 84 and the staple firing trigger 86, the deployment pins 136 travel along the final curved cam track section 358 of the cam slots 140. With the stapling head assembly open, each pivot pin 158 is returned to the distal end of the upper section 161 of the corresponding Z-shaped guide slot 160 and each of the deployment pins 136 is moved to the distal end of the curved cam track section 358 of the corresponding cam slot 140.

In order to reset the stapling instrument 50, after a test firing at the factory, the jaw closure lever 84 and the staple firing trigger 86 are moved into the closed position and the detents 360 are disengaged from the apertures 362 to allow the staple firing trigger 86 to move forward relative to the jaw closure lever 84 into the deployment position. Thereafter, the jaw closure lever 84 is moved forward to its open position and the staple firing trigger 86 is returned to its substantially horizontal inoperative position.

During the actuation of the stapling head assembly 60, firing forces are transmitted from the actuator handle assembly 80 to the stapling head assembly 60 via the firing cable 148. The geometry of the firing cable 148, the firing trigger plate 126, the cable pulley 120 and the closure lever pivot 110 is selected such that, during the closure and deployment of the staple firing trigger 86, the cable length remains substantially constant. To fire the stapling instrument 50, the staple firing trigger 86 is deployed by actuating the jaw closure lever 84 to its partially closed position. Then the firing safety lever 88 is disengaged from the staple firing trigger 86. By pulling the staple firing trigger 86, the firing cable 148 is placed in tension so that the forces applied from the stapling firing plate 126 to the jaw closure plates 114 via the pivot pins 128 tend to pull the jaw closure lever 86 further closed. This safety feature precludes the possible opening of the jaw closure lever 84 during the firing of the staples 65 from the staple cartridge 64.

In the actuation of the stapling head assembly 60, the firing cam 324 is pulled downwardly by the firing cable 148 and the staple driver 320 is advanced by two cam mechanisms. First, the firing cam pins 326 travel in the firing cam slots 328 which are inclined downwardly and forwardly at an angle of 15° relative to the vertical axis 52. Second, the inclined cam surfaces 332 and 334 on the firing cam 324 and the staple driver 320, respectively, engage each other and result in further displacement of the staple driver as the firing cam 324 is pulled downwardly. This dual cam mechanism achieves a high mechanical advantage in a compact space. The geometry of the two cam mechanisms is such that the firing cam 324 and the staple driver 320 move into engagement at the flat cam surfaces 336 and 338 before the travel of the firing cam pins 326 in the firing cam slots 328 is completed. This arrangement allows the staple driving mechanism to operate with two mechanical advantages, i.e., a low mechanical advantage during the initial stroke when both cam mechanisms are engaged and a high mechanical advantage toward the end of the stroke when only the firing cam slots 328 are engaged. The changeover in the operation of the dual cam mechanisms occurs at a low point in the forming force/deflection curve for the staples. This operation effectively minimizes the firing cable force at all points in the firing stroke of the staple forming mechanism.

Referring to FIG. 18, the staple cartridge 64 comprises an elongated, generally rectangular housing 370, preferably made of plastic, which includes a plurality of staple receiving slots or pockets 372 arranged in one or more longitudinal rows. Preferably, the staple receiving pockets 372 are arranged in two longitudinal rows (FIG. 20) so that the rows of staples 65 are staggered relative to each other. As shown in FIG. 18, the anvil 68 comprises an elongated, channel-shaped member made of metal, e.g., stainless steel. The anvil 68 includes a pair of longitudinally extending rows of staple forming grooves 366 (FIG. 19) which are arranged in pairs aligned with the staple receiving pockets 372 in the staple cartridge 64. The grooves 366 are shaped to form the staples 65 into a B-shaped configuration when the staple driver 320 is advanced to drive the staples 65 against the anvil 68.

In the embodiment of the staple cartridge 64 shown in FIG. 20, the right-hand row has nine staple receiving pockets 372 and the left-hand row has ten pockets 372. It will be understood by persons skilled in the art that other arrangements of staple receiving pockets 372 can be employed. For example, the staple cartridge 64 may include a single row of staple receiving pockets 372, or three or more staggered rows of staple receiving pockets 372. Similarly, the anvil 68 can be modified to include a single row of staple forming grooves 366, or three or more rows of staple forming grooves 366.

Figure 24:
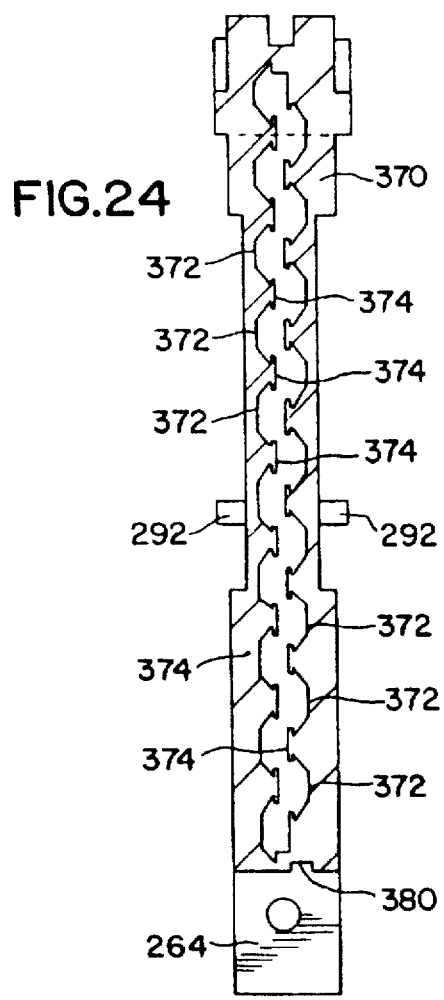
FIG. 24 is an enlarged vertical section of the staple cartridge along line 24—24 of FIG. 23.

As shown in FIG. 24, the staple receiving pockets 372 in each row are separated by a series of horizontal ribs 374 which serve as guides for the staples 65. The staple cartridge housing 370 includes a pair of elongated flanges 376 (FIG. 20) extending along its opposite sides. The flanges 376 are provided with longitudinal grooves 378 (FIG. 21) which serve as cutting guides for a surgical knife or scalpel. An elongated notch 380 (FIGS. 23 and 24) extends horizontally across the bottom of the staple cartridge housing 370 for receiving a corresponding ridge 382 (FIG. 19) formed on the spring housing 266 of the pilot member 250. The channel 380 and the ridge 382 act as a guide mechanism for aligning the anvil 68 with the staple cartridge 64 when the movable jaw 66 is pulled toward the fixed jaw 62.

Referring to FIGS. 25–28, the staple driver 320 includes a plurality of staple driving fingers 390 mounted on a central connecting web 392 and arranged in two staggered rows corresponding to the rows of staple receiving pockets 372 in the staple cartridge housing 370. The distal end of each staple driving finger 390 has a substantially hexagonal cross section and is slidably received in one of the staple forming pockets 372 which also has a substantially hexagonal shape. Each of the staple driving fingers 390 (FIG. 25) of the staple driver 320 is slidably received between an adjacent pair of ribs 374 (FIG. 24) on the staple cartridge housing 370. At its distal end, each of the staple driving fingers 390 has a pair of staple engaging ridges 394 (FIG. 27) separated by a transversely extending notch 396. A pair of staple receiving grooves 398 extends longitudinally across the ridges 394 on opposite sides of each notch 396.

Referring to FIGS. 28 and 29, a cam insert 400 can be sandwiched between the staple driving fingers 390 on the proximal side of the connecting web 392 to strengthen the staple driver 320. The proximal edge of the insert 400 has a pair of sloped cam surfaces 402 and a pair of flat cam surfaces 404 which are contoured to correspond to the cam surfaces 334 and 338 (FIGS. 27 and 28) at the proximal ends of the staple driving fingers 390 on the staple driver 320.

In the preferred embodiment of the surgical stapling instrument 50, the firing cable 148 and the closure cable 170 each have a counter-twisted construction which minimizes the changes in length of the cables 148 and 170 due to rotation of the support shaft assembly 70 about the longitudinal axis 54. The construction of the firing cable 148 and the closure cable 170 consists of multiple filaments or wires, preferably made of stainless steel, which are twisted together. A preferred embodiment of the cable construction is shown in FIGS. 46 and 47, which is equally applicable to both cables 148 and 170.

Figure 46:
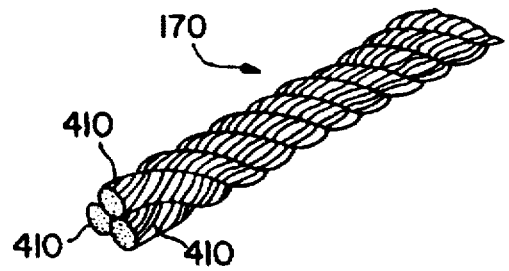
FIG. 46 is an enlarged perspective view showing the multiple strand construction of the cables of the stapling instrument.
Figure 47:
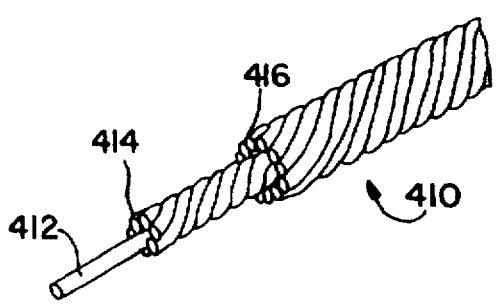
FIG. 47 is an enlarged perspective view showing the multiple filaments of each strand of the cables.

Referring to FIG. 46, the closure cable 170 has a multiple filament construction consisting of three multi-filament strands 410 which are twisted together in a helical arrangement with a right-hand twist. Each of the three strands 410 includes nineteen filaments or wires which are twisted together in a helical arrangement with a left-hand twist. As shown in FIG. 47, each strand 410 consists of a one-by-seven core comprising a center wire 412 covered by six wires 414 twisted in a left-hand direction about the center wire 412. A covering of twelve filaments or wires 416 is twisted in a left-hand direction about the one-by-seven core. The three strands 410, each including nineteen filaments or wires, are twisted together with a right-hand twist to provide a finished cable construction consisting of fifty-seven filaments or wires.

In the preferred embodiment, the center wire 412 is made of stainless steel, 0.0071 inch in diameter, ASTM F138-86 Grade 2. The six wires 414 are made of stainless steel, 0.0063 inch diameter, ASTM F138-86 Grade 2, twisted in a left-hand direction ("S" twist) about the center wire 412 in a range of 4.8 to 5.5 twists per inch. The twelve wires 416 are made of stainless steel, 0.0056 inch in diameter, ASTM F138-86 Grade 2, twisted in a left-hand direction ("S" twist) around the core in a range of 2.8 to 3.2 twists per inch. The finished cable consists of the three strands 410 of stainless steel wires which are twisted together in a right-hand direction ("Z" twist) in the range of 2.0 to 2.3 twists per inch.

The multi-filament, counter-twisted cable construction described above is insensitive to rotation so that the cables 148 and 170 maintain a substantially constant length when the support shaft assembly 70 is rotated about its longitudinal axis 54. The counter-wound construction of the multi-filament strands 410 tends to balance the shortening and lengthening effects on the cables 148 and 170 due to rotation of the shaft assembly 70 so that a substantially constant cable length is maintained within the ±170° rotational range of the support shaft assembly 70. For example, in the above cable construction, it is desired that the length of the cables 148 and 170 be maintained constant within ±0.005 inch over the ±170° range of rotation. Alternatively, if a conventional cable construction is used, a suitable cam surface (not shown) can be provided between the proximal end of the tubular shaft 74 and the stop plate 151 to compensate for changes in length of the cables 148 and 170 due to rotation of the support shaft assembly 70.

The invention in its broader aspects is not limited to the specific details of the preferred embodiments shown and described, and those skilled in the art will recognize that the invention can be practiced with modification within the spirit and scope of the appended claims.

We claim:

1. A surgical stapling instrument for applying one or more surgical staples to tissue, comprising:

a stapling head assembly including a proximal jaw which supports a staple holder for receiving one or more surgical staples, a distal law which supports an anvil for clamping the tissue against said staple holder when said jaws are closed, and a staple driver for driving the staples from said staple holder into the tissue and against said anvil;

an actuator handle assembly including a jaw closure lever for closing said jaws to move said anvil into a tissue clamping position and a staple firing trigger for actuating said staple driver;

a shaft assembly for mounting said stapling head assembly on said actuator handle assembly, said shaft assembly having proximal and distal ends and describing a longitudinal axis;

a closure cable connecting said distal jaw to said jaw closure lever and extending through said shaft assembly for pulling said distal jaw toward said proximal law when said jaw closure lever is actuated;

a firing cable connecting said staple driver to said staple firing trigger and extending through said shaft assembly for actuating said staple driver when said staple firing trigger is actuated;

a pivot connection at the distal end of said shaft assembly for supporting said stapling head assembly to pivot about a pivot axis transverse to the longitudinal axis of said shaft assembly;

said jaw closure cable being slidably received in said pivot connection and extending therethrough transversely to said pivot axis; and said pivot connection including means for providing a path of substantially constant length for said closure cable as said stapling head assembly pivots relative to said shaft assembly; and wherein:

each of said cables has a multi-filament counter-twisted construction to resist changes in length when said shaft assembly is rotated about its axis.

2. The stapling instrument of claim 1, wherein said pivot connection comprises:

a pivot housing mounted at the distal end of said shaft assembly and a pivot pin mounted in said pivot housing for pivotal movement about said pivot axis;

said pivot pin including a passage extending therethrough transversely to said pivot axis for slidably receiving said closure cable; and said passage having curved walls to maintain said closure cable along a path of substantially constant length as said stapling head assembly is pivoted to different angular positions.

3. The stapling instrument of claim 1, wherein:

said shaft assembly is rotatable about its axis to orient said stapling head assembly in different angular orientations relative to said actuator handle assembly.

4. The stapling instrument of claim 1, wherein:

said closure and said firing cables are each adapted to maintain a substantially constant length when said shaft assembly is rotated about its axis.

5. The stapling instrument of claim 1, wherein:

each of said cables comprises a plurality of multi-filament strands twisted together in a first helical direction; and each of said strands comprises a plurality of filaments twisted together in a second helical direction opposite to said first helical direction.

6. A surgical instrument for applying one or more surgical fasteners to tissue, comprising:

a fastener applying assembly including a proximal jaw which supports a fastener holder for receiving one or more surgical fasteners, a distal jaw which supports an anvil for clamping the tissue against said fastener holder when said jaws are closed, and a staple driver for driving the fasteners from said fastener holder into the tissue and against said anvil;

an actuator handle assembly including a first lever for closing said jaws to move said anvil into a tissue clamping position and a second lever for actuating said driver;

a shaft assembly for mounting said fastener applying assembly on said actuator handle assembly, said shaft assembly being rotatable about its longitudinal axis to orient said fastener applying assembly in different angular orientations relative to said actuator handle assembly;

a closure cable connecting said movable jaw to said jaw closure lever and extending through said shaft assembly for pulling said movable jaw toward said fixed jaw when said jaw closure lever is actuated;

a firing cable connecting said staple driver to a staple firing trigger and extending through said shaft assembly for actuating said staple driver when said staple firing trigger is actuated; and said closure cable being adapted to maintain its length substantially constant when said shaft assembly is rotated about its longitudinal axis; and wherein:

said closure cable has a multi-filament counter-twisted construction to resist changes in length when said shaft assembly is rotated about its axis.

7. The surgical instrument of claim 6, wherein:

said closure cable comprises a plurality of multi-filament strands twisted together in a first helical direction; and each of said strands comprises a plurality of filaments twisted together in a second helical direction opposite to said first helical direction.

8. The stapling instrument of claim 6, wherein:

said firing cable is adapted to maintain its length substantially constant when said shaft assembly is rotated about its longitudinal axis.

9. The surgical instrument of claim 6, wherein:

said firing cable has a multi-filament counter-twisted construction to resist changes in length when said shaft assembly is rotated about its axis.

10. The surgical instrument of claim 6, wherein:

said firing cable comprises a plurality of multi-filament strands twisted together in a first helical direction; and each of said strands comprises a plurality of filaments twisted together in a second helical direction opposite to said first helical direction.

* * * * *